US008629242B2

(12) United States Patent
Vitek et al.

(10) Patent No.: US 8,629,242 B2
(45) Date of Patent: Jan. 14, 2014

(54) METHODS OF INHIBITING CALCINEURIN WITH APOE ANALOGS

(75) Inventors: Michael P. Vitek, Cary, NC (US);
Feng-Qiao Li, Chapel Hill, NC (US)

(73) Assignee: Cognosci, Inc., Research Triangle Park, CA (US)

( * ) Notice: Subject to any disclaimer, the term of this patent is extended or adjusted under 35 U.S.C. 154(b) by 660 days.

(21) Appl. No.: 12/671,433

(22) PCT Filed: Jul. 31, 2008

(86) PCT No.: PCT/US2008/071815
§ 371 (c)(1),
(2), (4) Date: Jun. 24, 2010

(87) PCT Pub. No.: WO2009/018477
PCT Pub. Date: Feb. 5, 2009

(65) Prior Publication Data
US 2010/0305024 A1 Dec. 2, 2010

Related U.S. Application Data

(60) Provisional application No. 60/953,043, filed on Jul. 31, 2007.

(51) Int. Cl.
*C07K 14/00* (2006.01)

(52) U.S. Cl.
USPC ............. 530/324; 530/300; 530/325; 514/8.3

(58) Field of Classification Search
USPC .................................... 530/324, 325; 514/8.3
See application file for complete search history.

(56) References Cited

U.S. PATENT DOCUMENTS

| | | | | |
|---|---|---|---|---|
| 5,863,529 | A | * | 1/1999 | Rodriguez .................... 424/85.2 |
| 7,399,747 | B1 | | 7/2008 | Clair et al. |
| 7,947,645 | B2 | | 5/2011 | Vitek et al. |
| 8,288,335 | B2 | | 10/2012 | Vitek et al. |
| 2002/0137681 | A1 | * | 9/2002 | Steinman et al. ................ 514/12 |
| 2003/0100508 | A1 | * | 5/2003 | Simon et al. .................... 514/14 |
| 2003/0236186 | A1 | * | 12/2003 | Blaschuk et al. ................. 514/9 |
| 2004/0006022 | A1 | * | 1/2004 | Strominger et al. ............ 514/12 |
| 2004/0014652 | A1 | | 1/2004 | Trouet et al. |
| 2004/0121958 | A1 | * | 6/2004 | O'Brien .......................... 514/12 |
| 2008/0287354 | A1 | * | 11/2008 | O'Brien et al. ................. 514/12 |

FOREIGN PATENT DOCUMENTS

| | | |
|---|---|---|
| WO | WO 2006/029028 A2 | 3/2006 |
| WO | WO 2008/080082 A2 | 7/2008 |

OTHER PUBLICATIONS

Stangel (Current Neurology and Neuroscience Reports, vol. 6, No. 3, pp. 229-235, 2006).*
Stangel (Progress in Neurobiology, vol. 68, No. 5, pp. 361-376, 2002).*
Deshayes (Cellular & Molecular Life Sciences 62, 1839-49, 2005).*
Abstract of Nottingham, Exp Neurol 177(1) 242-251, 2002.*
Cognosci, "Novel Therapeutic Compounds for Multiple Sclerosis," Available on-line at http://web.archive.org/we/20070626115527/http://www.cognosci.com/documents/ms_white_paper.pdf, Jun. 26, 2007.
Li et al., "Apolipoprotein E-Derived Peptides Ameliorate Clinical Disability and Inflammatory Infiltrates into the Spinal Cord in a Murine Model of Multiple Sclerosis," Journal of Pharmacology and Experimental Therapeutics, vol. 318: 956-965, 2006.
Sheng et al., "Persistent Administration of ApoE Peptide Improves Neurological Mouse Spinal Cord Injury," Anesthesiology, vol. 107: A1434, 2007.
Young, Lee. Written Opinion of the International Search Authority for PCT/US2008/071815, mailed Apr. 10, 2009.
Wang et al., "Apolipoprotein E (ApoE) Peptide Regulates Tau Phosphorylation via Two Different Signaling Pathways," Journal of Neuroscience Research, vol. 51: 658-665, 1998.
Drin et al., "Studies on the Internalization Mechanism of Cationic Cell-Penetrating Peptides," Journal of Biological Chemistry, vol. 278: 31192-31201, 2003.
Camilleri, European Supplementary Search Report for European Application No. 08796986.1, mailed Oct. 24, 2011 (14 pages).
Li et al.,"Apolipoprotein E-Mimetic Peptides Promote the Survival and Proliferation of Oligodendrocyte Precursor Cells In Vitro and Remyelination In Vivo," Poster Presentation, BioSymposia Conference "Stem Cells and CNS Regeneration," May 31, 2007.
Singh et al., "The apolipoprotein E-mimetic peptide COG112 inhibits the inflammatory response to Citrobacter rodentium in colonic epithelial cells by preventing NF-kappaB activation," Journal of Biological Chemistry, vol. 283: 16752-16761, 2008.

* cited by examiner

*Primary Examiner* — David Lukton
(74) *Attorney, Agent, or Firm* — Cooley LLP

(57) ABSTRACT

The present invention provides a method of modulating calcineurin activity in a cell by contacting the cell with at least one ApoE analog. Methods of treating various disorders associated with calcineurin activity using one or more ApoE analogs are also disclosed. In particular, the present invention provides a method of reducing demyelination and promoting remyelination in a subject. Methods of treating spinal cord or nerve injury in a subject are also described.

35 Claims, 19 Drawing Sheets

METHODS OF INHIBITING CALCINEURIN WITH APOE ANALOGS

CROSS-REFERENCE TO RELATED APPLICATIONS

This application is a national stage application of International Application No. PCT/US2008/071815, filed Jul. 31, 2008, which claims the benefit of U.S. Provisional Application Ser. No. 60/953,043, filed Jul. 31, 2007, which is herein incorporated by reference in its entirety.

This application claims the benefit of U.S. Provisional Application Ser. No. 60/953,043, filed Jul. 31, 2007, which is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COGO_018_01US_SubSeqList_2_ST25.txt, date recorded: Sept. 9, 2011, file size 34 kilobytes).

FIELD OF THE INVENTION

The invention relates to methods of inhibiting calcineurin activity with ApoE analogs. The invention also relates to methods of treating demyelinating disorders and spinal cord injury by modulating calcineurin activity.

BACKGROUND OF THE INVENTION

Calcineurin, also known as PP2B, is a calcium-dependent serine/threonine phosphatase that plays a pivotal role in the activation of T cells during the immune response. Calcineurin dephosphorylates the NFAT (nuclear factor of activated T cells) transcription factor, which causes a conformational change that reveals a nuclear localization signal. NFAT is then translocated to the nucleus where it induces transcription of a number of cytokines, such as interleukin-2, that orchestrate the immune response. Calcineurin is targeted by the immunosuppressant drugs, cyclosporin A and FK506. Thus, one approach to the design of immunosuppressant therapies for preventing transplant rejection and treating autoimmune disorders is the development of novel calcineurin inhibitors.

In addition to its role in activation of the immune response, calcineurin signaling has been implicated in a number of other functions, such as angiogenesis, learning and memory, schizophrenia, myocardial hypertrophy, skeletal muscle differentiation, apoptosis, intimal hyperplasia, and heart disease (Aramburu et al. (2004) EMBO reports, Vol. 5: 343-348; Bueno et al. (2002) Cardiovascular Research, Vol. 53: 806-821). In recent years, calcineurin has been identified as a mediator of calcium-dependent axon repulsion in the central nervous system induced by myelin-associated proteins. Such axon repulsion limits the ability of neuronal axons to regenerate after an injury to the spinal cord and thus prevents functional recovery. Furthermore, oligodendrocytes, which are the cells that myelinate the axons of the central nervous system, are particularly vulnerable to apoptosis following injury. Loss of these cells leads to demyelination and further loss of neuronal function (Liu et al. (1997) J. Neurosci., Vol. 17: 5395-5406). Calcineurin has been reported to promote apoptosis by activating the pro-apoptotic protein Bad through dephosphorylation (Wang et al. (1999) Science, Vol. 284: 339-343) Inhibition of calcineurin after spinal cord injury in rats has been shown to result in a fewer number of apoptotic oligodendrocytes, suggesting that calcineurin is a mediator of apoptosis in these cells (Nottingham et al. (2002) Exp. Neurol., Vol. 177: 242-251). Therefore, calcineurin activation exacerbates neuronal damage caused by spinal cord injury by promoting loss of oligodendrocytes and hindering regeneration of damaged axons by mediating axon repulsion mechanisms. Thus, there is a need for the development of novel calcineurin inhibitors for treating spinal cord injury.

Other conditions, such as ischemia and multiple sclerosis, are associated with apoptosis of oligodendrocytes and demyelination of nerve fibers. Inhibition of calcineurin would be an effective therapeutic approach for treating these diseases as well. In the case of multiple sclerosis, inhibition of calcineurin would not only enhance the survival of oligodendrocytes and reduce demyelination, but also suppress the inflammatory response, which is dysfunctional in this autoimmune disorder. Given that aberrant calcineurin signaling appears to be associated with abnormal cell function and various disease states, the development of agents that regulate this phosphatase could be effective therapeutics in treating a number of conditions.

SUMMARY OF THE INVENTION

The present invention is based, in part, on the surprising discovery that ApoE analogs directly interact with and inhibit calcineurin activity. Accordingly, the invention provides a method of modulating calcineurin activity in a subject comprising administering at least one ApoE analog to the subject.

In one embodiment, the invention provides a method of modulating calcineurin activity in a cell comprising contacting the cell with at least one ApoE analog. In another embodiment, calcineurin activity is inhibited following contact with the at least one ApoE analog. In another embodiment, NFAT-mediated transcription is reduced in the cell following contact with the at least one ApoE analog. The cell may be in vitro or in vivo.

In another embodiment, the cell is in a subject. In some embodiments, the subject suffers from an inflammatory condition, heart disease, a renal condition, a fungal infection, a pulmonary disorder or muscular dystrophy. In other embodiments, the subject has a transplanted organ or tissue. In another embodiment, the subject is at risk for restenosis.

The present invention also provides a method of promoting remyelination in a subject in need thereof. In one embodiment, the method comprises administering an effective amount of at least one ApoE analog to the subject, wherein myelination is enhanced in the subject following administration of the at least one ApoE analog. In another embodiment, the subject is suffering from a demyelinating disorder or condition. In another embodiment, the subject has a spinal cord or nerve injury. In some embodiments, the number of oligodendrocytes is increased in the subject following administration of the at least one ApoE analog. In other embodiments, the amount of neuronal inflammation is decreased in the subject following administration of at least one ApoE analog. Preferably, one or more symptoms of demyelination is reduced in the subject following administration of the at least one ApoE analog.

The present invention also encompasses a method of treating multiple sclerosis in a subject in need thereof comprising administering an effective amount of at least one ApoE analog to the subject. In one embodiment, the amount of myelination is increased in the subject following administration of the at least one ApoE analog. In another embodiment, the number of oligodendrocytes is increased in the subject following administration of the at least one ApoE analog. In still another embodiment, the amount of neuronal inflammation is decreased in the subject following administration of the at least one ApoE analog. One or more symptoms of multiple sclerosis is preferably reduced in the subject following administration of the least one ApoE analog.

The present invention provides a method of treating spinal cord injury or nerve injury in a subject in need thereof. In one embodiment, the method comprises administering an effective amount of at least one ApoE analog to the subject. The spinal cord injury may be a contusive injury or a compressive injury. In another embodiment, the nerve injury is a peripheral nerve crush injury. In another embodiment, axonal degeneration is decreased in the subject following administration of the at least one ApoE analog. In still another embodiment, inflammation at the injured site is decreased following administration of the at least one ApoE analog. Inflammation may include activation of microglia or macrophages as well as secretion of inflammatory cytokines.

The present invention also contemplates a method of promoting the survival and/or proliferation of oligodendrocyte precursor cells. In one embodiment, the method comprises treating the oligodendrocyte precursor cells with at least one ApoE analog, wherein the number of oligodendrocyte precursor cells is increased following treatment with the at least one ApoE analog. The treatment with the at least one ApoE analog may be in vitro or in vivo. In another embodiment, calcineurin activity is inhibited in the oligodendrocyte precursor cells following treatment with the at least one ApoE analog.

DETAILED DESCRIPTION OF THE INVENTION

Figure 1:
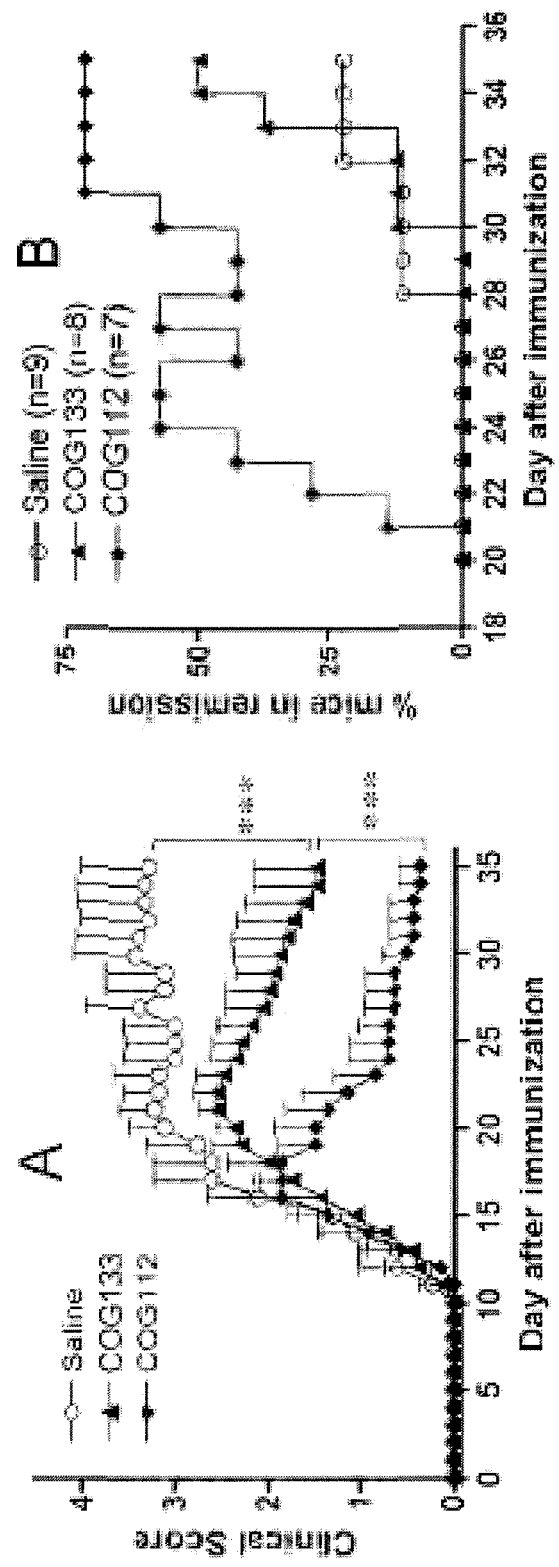
FIG. 1. COG 133 and COG 112 promote the recovery of animals from clinical disability of EAE when applied after the onset of disease. (A) Changes in the mean daily clinical score (CS) after treatment with COG 133 (1 mg/kg, i.p.) or COG 112 (1 mg/kg, i.p.). (B) Percentage of animals in remission. Statistical analysis was conducted by ANOVA comparing the CS after day 18, which was defined as the recovery phase.

Aberrant calcineurin signaling has been implicated in a number of disorders ranging from nerve injury to heart disease. The inventors have surprisingly discovered that ApoE analogs can bind directly to calcineurin and inhibit its activity. Therefore, ApoE analogs represent a novel therapeutic for treating a myriad of conditions associated with over-activation of calcineurin.

The present invention provides a method of modulating calcineurin activity in a cell. In one embodiment, the method comprises contacting the cell with at least one ApoE analog. As used herein, "modulating" refers to changes in calcineurin activity observed in vitro or in vivo, including an increase or decrease in calcineurin activity. As previously discussed, activation of calcineurin is reported to be involved in multiple biological processes associated with disease. For example, calcineurin is known to play a vital role in activation of the immune response and is a target for current therapies used to prevent transplant rejection. Calcineurin is also associated with other inflammatory conditions, such as autoimmune disorders, inflammatory skin conditions, and asthma. In addition, calcineurin signaling also appears to be important in neurological conditions, such as demyelinating disorders and the repair of the nervous system after injury.

Activation of calcineurin by any number of stimuli results in the dephosphorylation and activation of the nuclear factor of activated T cell (NFAT) family of transcription factors, which in turn stimulate transcription of interleukin-2 (IL2) and other cytokines. In one embodiment of the present invention, modulation of calcineurin in a cell by at least one ApoE analog results in inhibition of calcineurin activity. In another embodiment, NFAT-mediated transcription is reduced in the cell. In another embodiment, interleukin-2 expression is decreased in the cell.

Activities of calcineurin can be either direct activities or indirect activities. A direct activity of calcineurin occurs when calcineurin interacts directly with a substrate and dephosphorylates it, thereby causing an activation or inactivation of the substrate protein. An indirect activity of calcineurin occurs when a protein is affected by calcineurin activity although the protein is not a direct substrate for calcineurin. For instance, downstream molecules in signaling cascades can be indirectly affected by calcineurin as the result of activation or inactivation of upstream proteins in the cascade.

In one embodiment, the at least one ApoE analog for modulating calcineurin activity is a peptide derivative of COG 133 (LRVRLASHLRKLRKRLL; SEQ ID NO: 1). COG 133 is a truncated peptide comprised of residues 133-149 of ApoE and has previously proved useful in treating or reducing cerebral ischemia or cerebral inflammation. See U.S. application Ser. No. 10/252,120, filed Sep. 23, 2002, incorporated herein by reference in its entirety. In another embodiment of the invention, the ApoE analog may be a peptide derivative containing a sequence selected from the group consisting of:

```
                                            (SEQ ID NO: 2)
Ac-As-Aib-LRKL-Aib-KRLL-NH2

(SEQ ID NO: 3)
Ac-LRVRLAS-Aib-LRKLRK(nitro-Arg)LL-NH2, (SEQ ID NO: 4)
Ac-LRVRLAS-Aib-LRKLRK(acetyl-Arg)LL-NH2,
```

```
                                            (SEQ ID NO: 5)
Ac-RQIKIWFQNRRMKWKKCLRVRLASHLRKLRKRLL-NH2, (SEQ ID NO: 6)
Ac-Aib-LRKL-Aib-(n acetyl K)RLL-NH2,
and (SEQ ID NO: 7)
Ac-RRLSYSRRRFLRVRLASHLRKLRKRLL-NH2,
``` wherein Aib is amino iso-butyric acid, (nitro-Arg) is nitro arginine, (acetyl-Arg) is acetyl arginine, (n acetyl K) is n-acetyl lysine, and Ac is an acetylated amino terminus. The ApoE analog may be derived from a peptide containing residues 130-150 of the ApoE holoprotein. As used herein, "derived" means that the derivative contains the basic structure of the peptide from which it is derived, but has either one or more insertions, deletions, or substitutions in its amino acid sequence. Substitutions encompass non-natural amino acids as well as both conservative and non-conservative amino acid substitutions. The peptide derivative may retain the alpha-helical character of residues 130-150 of ApoE. Other suitable ApoE analogs that may be used in the methods of the invention include those described in WO 2006/029028, filed Sep. 2, 2005, which is herein incorporated by reference in its entirety. See Table 1.

In one embodiment of the invention, the efficacy of the ApoE peptide derivative can be improved by conjugation to a protein transduction domain (PTD). PTDs are short basic peptides that promote the intracellular delivery of cargo that would otherwise fail to, or only minimally, traverse the cell membrane. PTDs can be used to enhance CNS penetration of compounds. For instance, empirical testing of PTDs can be performed to identify PTDs that are capable of transporting cargo across the blood brain barrier. PTDs can be antimicrobial peptides, such as protegrin 1, Bactenecin 7, Buforin, and Maginin; a host of arginine-rich RNA- and DNA-binding peptides (e.g., HIV-1 transactivating protein (TAT) and *Drosophila* homeodomain transcription factor Antennapedia (a.k.a. Penetratin); chimeric PTDs such as Transportan; lysine- and arginine-rich peptides derived from phage-display libraries; polyarginine; and β-homolysine oligomers (See, Fisher et al. (2001) Bioconjugate Chemistry, Vol. 12: 825-841; Lindsay (2002) Current Opinions in Pharmacology, Vol. 2: 587-594; Tung and Weissleder (2003) Advanced Drug Delivery Reviews, Vol. 55: 281-294; Liefert and Whitton (2003) Molecular Therapy, Vol. 8: 13-19; Bogoyevitch et al. (2002) DNA and Cell Biology, Vol. 21: 879-894; and Garcia-Echeverria and Ruetz (2003) Bioorganic and Medicinal Chemistry Letters, Vol. 13: 247-251, all of which are incorporated by reference in their entireties). In some embodiments, the ApoE peptide derivative is conjugated to a protein transduction domain selected from the group consisting of peptides derived from antennapedia, TAT, SynB1, SynB3, SynB5, and polyarginine. For example, COG 112 (SEQ ID NO: 5) and COG 68 (SEQ ID NO: 7) are ApoE peptides linked to PTDs. COG 112 is linked to antennapedia, while COG 68 is linked to SynB3. Such PTD peptides may comprise a sequence selected from the group consisting of:

```
GRKKRRQRRRPPQ          (SEQ ID NO: 9)

RQIKIWFQNRRMKWKK       (SEQ ID NO: 10)

RRMKWKK                (SEQ ID NO: 11)
```

```
RGGRLSYSRRRFSTSTGR      (SEQ ID NO: 12)

RRLSYSRRRF              (SEQ ID NO: 13)

RGGRLAYLRRRWAVLGR       (SEQ ID NO: 14)

RRRRRRRR.               (SEQ ID NO: 15)
```

ApoE analogs suitable for use in the methods of the present invention can be produced by standard techniques as are known in the art. In some embodiments, the ApoE analogs may be peptide derivatives. Modification of the peptide derivatives disclosed herein to enhance the functional activities associated with these peptides could be readily accomplished by those of skill in the art. For instance, the peptides used in the methods of the present invention can be chemically modified or conjugated to other molecules in order to enhance parameters like solubility, serum stability, etc, while retaining functional activity. In particular, the peptides of the invention may be acetylated at the N-terminus and/or amidated at the C-terminus, or conjugated, complexed or fused to molecules that enhance serum stability, including but not limited to albumin, immunoglobulins and fragments thereof, transferrin, lipoproteins, liposomes, α-2-macroglobulin and α-1-glycoprotein, PEG, lipids, and dextran. Such molecules are described in detail in U.S. Pat. No. 6,762,169, which is herein incorporated by reference in its entirety. Small molecules that target the conjugate to specific cells or tissues may also be used. It is known that presence of a biotin-avidin complex increases uptake of such modified peptides across endothelial cells. Linkage of peptides to carbohydrate moieties, for example to a β-glycoside through a serine residue on the peptide to form β-0-linked glycoside, enhances transport of the glycoside derivative via glucose transporters (Polt, R. et al. Proc. Natl. Acad. Sci. USA 91: 7144-7118 (1994); Oh et al. Drug Transport and targeting, In Membrane Transporters as Drug Targets, Amidon, G. L. and Sadee, W. eds., pg 59-88, Plenum Press, New York, 1999). The peptides may have attached various label moieties such as radioactive labels, heavy atom labels, and fluorescent labels for detection and tracing. Fluorescent labels include, but are not limited to, luciferin, fluorescein, eosin, Alexa Fluor, Oregon Green, rhodamine Green, tetramethylrhodamine, rhodamine Red, Texas Red, coumarin and NBD fluorophores, the QSY 7, dabcyl and dabsyl chromophores, BODIPY, Cy5, etc.

Another variation of the ApoE analogs of the present invention is the linking of from one to fifteen amino acids or analogs to the N-terminal or C-terminal amino acid of the peptide derivatives disclosed herein. Analogs of the peptide derivatives can also be prepared by adding from one to fifteen additional amino acids to the N-terminal, C-terminal, or both N- and C-terminals, of an active peptide, where such amino acid additions do not adversely affect the ability of the peptide to bind to calcineurin and modulate its activity. For example, COG 1410 (SEQ ID NO: 2), COG 248 (SEQ ID NO: 3), COG 345 (SEQ ID NO: 4), COG 112 (SEQ ID NO: 5), COG 241 (SEQ ID NO: 6), and COG 68 (SEQ ID NO: 7) variants can be created by adding from one to fifteen additional amino acids to the N-terminal, C-terminal, or both N- and C-terminals, of the active peptide. An active peptide is any peptide capable of binding to calcineurin and modulating calcineurin activity.

The ApoE analogs of the present invention further include conservative variants of the peptides herein described. As used herein, a conservative variant refers to alterations in the amino acid sequence that do not adversely affect the biological functions of the peptide. A substitution, insertion or deletion is said to adversely affect the peptide when the altered sequence prevents or disrupts a biological function associated with the peptide. For example, the overall charge, structure or hydrophobic/hydrophilic properties of the peptide may be altered without adversely affecting a biological activity. Accordingly, the amino acid sequence can be altered, for example to render the peptide more hydrophobic or hydrophilic, without adversely affecting the biological activities of the peptide. Ordinarily, the conservative substitution variants, analogs, and derivatives of the peptides, will have an amino acid sequence identity to the disclosed sequences SEQ ID NOs: 1-7 of at least about 55%, at least about 65%, at least about 75%, at least about 80%, at least about 85%, at least about 90%, at least about 95%, or at least about 96% to 99%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology. Thus, the ApoE analogs of the present invention include peptide derivatives having the amino acid sequence disclosed in SEQ ID NOs: 1-7; fragments thereof having a consecutive sequence of at least about 3, 4, 5, 6, 10, 15, or more amino acid residues of the peptide; amino acid sequence variants of such peptides wherein an amino acid residue has been inserted N- or C-terminal to, or within, the disclosed sequence; and amino acid sequence variants of the disclosed sequence, or their fragments as defined above, that have been substituted by another residue. Peptide compounds comprising the peptide sequences of the invention may be 15, 20, 25, 30, 35, 40, 45, 50 or more amino acids. Contemplated variants further include those containing predetermined mutations by, e.g., homologous recombination, site-directed or PCR mutagenesis, and the corresponding peptides of other animal species, including but not limited to rabbit, rat, porcine, bovine, ovine, equine and non-human primate species, and derivatives wherein the peptide has been covalently modified by substitution, chemical, enzymatic, or other appropriate means with a moiety other than a naturally occurring amino acid (for example a detectable moiety such as an enzyme or radioisotope).

ApoE analogs capable of modulating calcineurin activity, including but not limited to peptide derivatives of COG 133 (SEQ ID NO: 1), can be in free form or the form of a salt, where the salt is pharmaceutically acceptable. These include inorganic salts of sodium, potassium, lithium, ammonium, calcium, magnesium, iron, zinc, copper, manganese, and the like. Various organic salts of the peptide derivatives may also be made with, including, but not limited to, acetic acid, propionic acid, pyruvic acid, maleic acid, succinic acid, tartaric acid, citric acid, benozic acid, cinnamic acid, salicylic acid, etc.

The present invention contemplates a method of modulating calcineurin activity in a cell by contacting the cell with at least one ApoE analog in vivo. In one embodiment, the cell is in a subject. The subject may suffer from an inflammatory condition, heart disease, a renal condition, a fungal infection, a pulmonary disorder, or muscular dystrophy. Accordingly, the present invention provides methods of treating these disorders in a subject in need thereof by administering at least one ApoE analog to the subject. In preferred embodiments, the ApoE analog is a peptide derivative having the sequence of SEQ ID NO: 2, SEQ ID NO: 3, SEQ ID NO: 4, SEQ ID NO: 5, SEQ ID NO: 6 or SEQ ID NO: 7.

As discussed above, calcineurin signaling is instrumental in the activation of the immune response. As such, calcineurin is an attractive therapeutic target for designing treatments for inflammatory conditions. Several calcineurin inhibitors are currently available as immunosuppressants for preventing organ transplant rejection and treating autoimmune disorders. In addition, inhibition of calcineurin has previously shown to be an effective treatment for inflammatory skin conditions including atopic dermatitis (eczema), facial and intertriginous psoriasis, hand dermatitis, lichen planus, and vitiligo (leukoderma) among others. The inventive methods of modulating calcineurin in a cell by contacting the cell with at least one ApoE analog can be used to ameliorate one or more symptoms associated with an inflammatory condition. In one embodiment, the inflammatory condition is an inflammatory skin condition, such as those described above. In another embodiment, the inflammatory condition is asthma. In another embodiment, the inflammatory condition is an autoimmune disorder. Non-limiting examples of autoimmune disorders include rheumatoid arthritis, myasthenia gravis, systemic lupus erythematosus, psoriasis, multiple sclerosis, ulcerative colitis, Crohn's disease, and diabetes (type 1).

In another embodiment, the methods of the invention may be used to prevent rejection of transplanted organs or tissues in a subject. Rejection of transplanted tissues occurs because the immune system of the recipient attacks the donor organ or tissue. Transplant recipients are typically administered an immunosuppressant, such as a calcineurin inhibitor, to reduce the immune response to the foreign tissue. Thus, at least one ApoE analog may be administered to the subject to suppress calcineurin activation and prevent transplant rejection. ApoE analogs, such as COG 1410 (SEQ ID NO: 2), COG 248 (SEQ ID NO: 3), COG 345 (SEQ ID NO: 4), COG 112 (SEQ ID NO: 5), COG 241 (SEQ ID NO: 6), and COG 68 (SEQ ID NO: 7) may be administered to subjects receiving any type of organ or tissue transplant, such as heart, lung, liver, kidney, pancreas, intestine, skin graft, cornea, bone marrow, heart valve, blood vessels, and bone.

Calcineurin activation has also been linked to various forms of heart disease, such as myocardial infarction, dilated cardiomyopathy, pathologic cardiac hypertrophy, and heart failure (see, for example, Bueno et al. (2002) Cardiovascular Research, Vol. 53: 806-821 and Mitsuhashi et al. (2003) J. Biol. Chem., Vol. 134: 269-276). Administration of at least one ApoE analog to a subject can reduce or prevent one or more symptoms of heart disease. In one embodiment, the heart disease is pathologic cardiac hypertrophy, dilated cardiomyopathy, or heart failure.

In addition to its involvement in diseases of cardiac muscle, calcineurin is known to regulate gene expression in skeletal muscle, such as genes related to fiber-type switching. Genetic deletion of calcineurin in skeletal muscles of scgd -/- mice, a mouse model of limb-girdle muscular dystrophy, reduced skeletal muscle degeneration and pathology, suggesting calcineurin signaling may mediate, in part, the skeletal muscle pathogenesis observed in the disease (Parsons et al. (2007) J. Biol. Chem., Vol. 282: 10068-10078). ApoE analogs may be an effective treatment for muscular dystrophy by inhibiting calcineurin activity, and thus ameliorating skeletal muscle degeneration.

Modulation of calcineurin activity by ApoE analogs may also be effective in treating several renal conditions Inhibition of calcineurin activity was shown to decrease renal hypertrophy in diabetic rats (Gooch et al. (2003) Am. J. Physiol. Renal Physiol., Vol. 284: F144-F154). Renal hypertrophy is often a harbinger of several pathological conditions. As such, reduction of renal hypertrophy may prevent the development of more serious renal complications. The present invention contemplates a method of treating a renal condition in a subject in need thereof comprising administering at least one ApoE analog to the subject. In one embodiment, the renal condition is diabetic nephropathy or renal hypertrophy.

Disruption of the endothelial barrier leading to tissue edema underlies many acute inflammatory diseases of the lung. Calcineurin has been implicated in the control of endothelial barrier function and the subsequent development of pulmonary edema. Regulation of calcineurin activity by ApoE analogs according to the methods of the present invention provide a therapeutic approach to treating pulmonary disorders, such as pulmonary edema and respiratory failure, in a subject.

In another embodiment, the present invention provides a method for treating a fungal infection in a subject comprising administering at least one ApoE analog capable of modulating calcineurin activity in a cell of the subject. *Candida albicans*, a yeast-like fungi, is one of the most frequent causes of keratitis, which can progress to endophthalmitis posing a risk for loss of vision. Calcineurin activity appears to be required for survival of *C. albicans*, especially in the presence of standard anti-fungal azole drugs. Thus, ApoE analogs administered alone or in combination with other anti-fungal treatments, may alleviate fungal infections caused by drug-resistant strains.

In yet another embodiment, the present invention provides a method of preventing restenosis in a subject comprising administering at least one ApoE analog capable of modulating calcineurin activity in a cell of the subject. Restenosis is the re-narrowing of a blood vessel, which is a common occurrence after vascular surgery or angioplasty to open a blocked artery or vessel. One cause of restenosis is intimal hyperplasia induced by inflammatory cytokines stimulated by injury to the vessel as a result of the vascular procedure Inhibition of calcineurin in combination with an anti-proliferative therapy has been shown to produce a synergistic reduction in intimal thickening after angioplasty in rats. In addition, tacrolimus, a calcineurin inhibitor, was reported to inhibit the proliferation of vascular smooth muscle cells and prevent restenosis in clinical trials. In one embodiment, ApoE analogs, such as COG 1410 (SEQ ID NO: 2), COG 248 (SEQ ID NO: 3), COG 345 (SEQ ID NO: 4), COG 112 (SEQ ID NO: 5), COG 241 (SEQ ID NO: 6), and COG 68 (SEQ ID NO: 7) may be used to coat stents that can be placed in vessels after angioplasty or other vascular surgical procedure to prevent the development of intimal hyperplasia and subsequent restenosis. Alternatively or additionally, ApoE analogs may be administered alone or with anti-proliferative drugs, such as sirolimus, to the subject after a vascular procedure to prevent restenosis of the unblocked vessel.

Recently, calcineurin has been identified to play a role in demyelination of axons. Oligodendrocytes, which myelinate the axons of the central nervous system, are susceptible to apoptosis following neuronal injury. Loss of oligodendrocytes causes demyelination and neuronal dysfunction (Liu et al. (1997) J. Neurosci., Vol. 17: 5395-5406) Inhibition of calcineurin following spinal cord injury was shown to result in fewer apoptotic oligodendrocytes indicating that calcineurin activation promotes apoptosis in these cells (Nottingham et al. (2002) Exp. Neurol., Vol. 177: 242-251). Thus, modulation of calcineurin activity by contacting oligodendrocytes with at least one ApoE analog would promote the survival of oligodendrocytes and prevent demyelination following injury. In fact, the inventors have demonstrated that ApoE analogs enhance the survival of both oligodendrocyte precursor cells as well as mature oligodendrocytes in vivo and in vitro (See Examples 3-5). Furthermore, ApoE holoprotein has been implicated in remyelination after nerve injury due to its role in lipid transport. Thus, the present invention provides a method of promoting remyelination in a subject in need thereof. In one embodiment, the method comprises administering an effective amount of at least one ApoE analog to the subject, wherein myelination is enhanced in the subject following administration of the at least one ApoE analog.

An effective amount of at least one ApoE analog is an amount that increases myelination in a subject as compared to that which would occur in the absence of the analog. In one embodiment, the effective amount of an ApoE analog increases the number of oligodendrocyte precursor cells or mature oligodendrocytes compared to that which would occur in the absence of the analog. In another embodiment, the effective amount of an ApoE analog is an amount that modulates calcineurin activity in a subject. The effective amount (and the manner of administration) will be determined on an individual basis and will be based on the specific agent being used and a consideration of the subject (size, age, general health), the condition being treated, the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the ApoE analogs described herein can be determined using in vitro tests, animal models or other dose-response studies, as are known in the art.

In another embodiment, the method comprises administering an effective amount of at least one ApoE analog to promote remyelination in a subject suffering from a demyelinating disorder or condition. Demyelinating disorders or conditions include, but are not limited to, optic neuritis, devic disease, transverse myelitis, acute disseminated encephalomyelitis, adrenoleukodystrophy, adrenomyeloneuropathy, multiple sclerosis, Guillain-Barre syndrome, Chronic Inflammatory Demyelinating Polyneuropathy (CIDP), and diabetic peripheral neuropathy. In another embodiment, the subject in need of remyelination has a spinal cord or nerve injury.

Any of the ApoE analogs described herein are suitable for use in the method of promoting remyelination in a subject. In one embodiment, the at least one ApoE analog is a peptide derivative of COG 133 (SEQ ID NO: 1). In preferred embodiments, the peptide derivative contains a sequence selected from the group consisting of COG 1410 (SEQ ID NO: 2), COG 248 (SEQ ID NO: 3), COG 345 (SEQ ID NO: 4), COG 112 (SEQ ID NO: 5), COG 241 (SEQ ID NO: 6), and COG 68 (SEQ ID NO: 7). In another embodiment, the number of oligodendrocytes is increased in the subject following administration of the at least one ApoE analog. In still another embodiment, the amount of neuronal inflammation is decreased in the subject following administration of the at least one ApoE analog. In yet another embodiment of the invention, one or more symptoms of demyelination is reduced in the subject following administration of the at least one ApoE analog. Symptoms of demyelination include, but are not limited to, conduction block, conduction slowing, numbing, tingling, pain, progressive muscle weakness, loss of deep tendon reflexes (areflexia), fatigue, abnormal sensations, and paralysis.

The present invention also encompasses a method of treating spinal cord injury or nerve injury in a subject in need thereof comprising administering an effective amount of at least one ApoE analog to the subject. In one embodiment, the spinal cord injury is a contusive injury or a compressive injury. In another embodiment, the nerve injury is a peripheral nerve crush injury. Preferably, the ApoE analog is administered shortly after the occurrence of the spinal cord or nerve injury, such as within 1 hour, 2 hours, 3, 4, 5, 6, 7, 8, 9, 10 hours, 18 hours, 24, hours, 36 hours, or 48 hours after the injury.

Axonal degeneration typically occurs after spinal cord or nerve injury. When a nerve fiber is cut or crushed, the part distal to the injury (i.e. the part of the axon separated from the neuron's nucleus) will degenerate. This process typically commences within 24 hours of a lesion. Axonal degeneration is followed by loss of the myelin sheath (i.e. demyelination) and infiltration by macrophages, which scavenge the cellular debris left by the degenerating axons. The loss of axons is the cause of the loss of neuronal function (e.g. motor and sensory function) below the level of the injury. In one embodiment, axonal degeneration is decreased in the subject following administration of the at least one ApoE analog. In another embodiment, inflammation at the injured site is decreased following administration of the at least one ApoE analog. Inflammation may include the activation of microglia or macrophages as well as the release of inflammatory cytokines. Any of the ApoE analogs described herein may be used in treating spinal cord or nerve injury in a subject.

The present invention also provides a method of promoting the survival and/or proliferation of oligodendrocyte precursor cells. In one embodiment, the method comprises treating the oligodendrocyte precursor cells with at least one ApoE analog, wherein the number of oligodendrocyte precursor cells is increased following treatment with the at least one ApoE analog. The treatment with the at least one ApoE analog may be in vitro or in vivo. Methods of detection and quantification of oligodendrocyte precursor cells are known in the art. Such methods include, but are not limited to, immunohistochemistry, in situ hybridization, cell sorting (e.g. FACS), and enzymatic assays. Oligodendrocye precursor cells as well as mature oligodendrocytes can be identified by one or more proteins that are specifically expressed in these cell types (i.e. markers). Some non-limiting examples of oligodendrocyte markers include the ganglioside GD3, the NG2 chondroitin sulfate proteoglycan, platelet-derived growth factor-alpha receptor subunit (PDGF-alphaR), glutathione S-transferase, and 2',3'-Cyclic Nucleotide 3'-Phosphodiesterase (CNPase).

In another embodiment, calcineurin activity is inhibited in the oligodendrocyte precursor cells following treatment with the at least one ApoE analog. Methods of measuring calcineurin phosphatase activity are known in the art and include, but are not limited to, in vitro phosphorylation assays that monitor release of phosphate from a peptide substrate, and western blot methods that detect phosphorylation status of endogenous substrates in cellular lysates. In some embodiments, the at least one ApoE analog is a peptide derivative of COG 133 (SEQ ID NO: 1). The peptide derivative may contain a sequence of COG 1410 (SEQ ID NO: 2), COG 248 (SEQ ID NO: 3), COG 345 (SEQ ID NO: 4), COG 112 (SEQ ID NO: 5), COG 241 (SEQ ID NO: 6), or COG 68 (SEQ ID NO: 7).

Multiple sclerosis is an autoimmune disease that is one of the most common neurological diseases in young adults and affects more than 2 million people worldwide. Multiple sclerosis is characterized by inflammation and demyelination of the brain and spinal cord accompanied by extensive depletion of oligodendrocytes and axonal degeneration. Current therapies for multiple sclerosis target the inflammation associated with the disease rather than restoring myelination. Increased expression of ApoE protein, known for its role in lipid metabolism, is reported to occur at sites of active remyelination. Furthermore, levels of ApoE protein in the cerebrospinal fluid of multiple sclerosis patients proved to be a reliable marker of patients in remission (Rifai et al. (1987) Clin. Chem., Vol. 33: 1155-1157). Given that ApoE analogs promote the survival of oligodendrocyte precursor cells and oligodendrocytes as well as enhance remyelination of demyelinated axons (see Examples 3-5), ApoE analogs may be an effective treatment for multiple sclerosis. In fact, the inventors demonstrated that ApoE analogs could promote remyelination in an experimental autoimmune encephalomyelitis (EAE) model of human multiple sclerosis (MS) and this remyelination correlated with recovery from clinical symptoms of the disease (see Example 1).

The present invention contemplates a method of treating multiple sclerosis in a subject in need thereof comprising administering an effective amount of at least one ApoE analog to the subject. ApoE analogs suitable in the inventive method include those ApoE analogs described herein. In some embodiments, the ApoE analog is a peptide derivative containing a sequence selected from the group consisting of COG 248 (SEQ ID NO: 3), COG 345 (SEQ ID NO: 4), COG 241 (SEQ ID NO: 6), and COG 68 (SEQ ID NO: 7). In a preferred embodiment, the ApoE peptide derivative contains the sequence of COG 345 (SEQ ID NO: 4). The ApoE peptide derivatives may be conjugated to a protein transduction domain as described herein to facilitate transport across the blood brain barrier and access to the central nervous system. In another embodiment, the amount of myelination is increased in the subject following administration of the at least one ApoE analog. In another embodiment, the number of oligodendrocytes is increased in the subject following administration of the at least one ApoE analog. In still another embodiment, the amount of neuronal inflammation is decreased in the subject following administration of the at least one ApoE analog. Neuronal inflammation may be measured by the number of inflammatory cells infiltrating central nervous system tissue as well as by activation of microglia and macrophages.

In another embodiment of the invention, one or more symptoms of multiple sclerosis is reduced in the subject following administration of the at least one ApoE analog. Symptoms of multiple sclerosis include, but are not limited to, changes in sensation (hypoesthesia), muscle weakness, abnormal muscle spasms, difficulty in moving, difficulties with coordination and balance (ataxia), problems in speech (dysarthria) or swallowing (dysphagia), visual problems (nystagmus, optic neuritis, or diplopia), fatigue and acute or chronic pain syndromes, and bladder and bowel difficulties. Cognitive impairment of varying degrees, or emotional symptoms in the form of depression or pseudobulbar affect are also common. Neuropathic pain, described as constant, boring, burning or tingling intensely, is typical and usually occurs in the legs. Other symptoms of multiple sclerosis include paraesthesias, such as pins and needles, tingling, shivering, burning pains, feelings of pressure, and areas of skin with heightened sensitivity to touch.

In some embodiments, the ApoE analogs of the present invention are used in combination with a pharmaceutically acceptable carrier. The present invention thus also provides pharmaceutical compositions suitable for administration to a subject. Such compositions comprise an effective amount of an ApoE analog as described herein in combination with a pharmaceutically acceptable carrier. The carrier can be a liquid, so that the composition is adapted for parenteral administration, or can be solid, i.e., a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. ApoE analogs can alternatively be formulated for encapsulation in liposomes, using known methods. Additionally, the intranasal administration of peptides to treat CNS conditions is known in the art (see, e.g., U.S. Pat. No. 5,567,682, incorporated herein by reference to Pert, regarding intranasal administration of peptide T to treat Alzheimer's Disease). Preparation of an ApoE analog of the present invention for intranasal administration can be carried out using techniques as are known in the art. Pharmaceutical preparations of the agents of the present invention can optionally include a pharmaceutically acceptable diluent or excipient.

An alternative method of administering ApoE analogs, such as peptide derivatives, of the present invention is carried out by administering to the subject a vector carrying a nucleic acid sequence encoding the peptide derivative, where the vector is capable of entering cells of the body, such as cells of the central nervous system, heart, kidney, and lung, so that the peptide derivative is expressed and secreted. In particular, expression of peptide derivatives in the brain and spinal cord make the ApoE peptide derivatives available to microglial cells and oligodendrocytes. Suitable vectors are typically viral vectors, including DNA viruses, RNA viruses, and retroviruses. Techniques for utilizing vector delivery systems and carrying out gene therapy are known in the art. Herpesvirus vectors, adenovirus vectors, adeno-associated virus vectors and lentiviral vectors are particular types of vectors that can be employed in administering compounds of the present invention.

In another embodiment, an ApoE analog of the invention may be formulated for topical administration, particularly in the treatment of inflammatory skin conditions, such as atopic dermatitis (eczema), psoriasis, hand dermatitis, lichen planus, and vitiligo (leukoderma). The topical formulation may be a cream, gel, ointment, lotion, paste, spray, or powder. Pharmaceutical carriers for topical formulations include aqueous, powder or oily bases, thickeners, emulsifiers, semi-solid preparations of hydrocarbons (petrolatum, mineral oil, paraffins, synthetic hydrocarbons), surfactants, emollients and the like. Other suitable carriers and ingredients for topical formulations are discernible to one skilled in the art.

In another embodiment, an ApoE analog as described herein may be formulated as a coating for a medical device, such as a stent or catheter. Particularly useful in methods of treating restenosis in a subject, the ApoE analog may be used to coat a metal stent to produce a drug-eluting stent. A drug-eluting stent is a scaffold that holds open narrowed or diseased arteries and releases a compound to prevent cellular proliferation and/or inflammation. ApoE analogs may be applied to a metal stent imbedded in a thin polymer for release of the ApoE analog over time. Methods of coating stents with therapeutic compounds are known in the art. See, e.g., U.S. Pat. Nos. 7,144,422; 7,055,237; and WO 2004/004602, which are here incorporated by reference in their entireties. In some embodiments, the ApoE analog may be used in combination with other anti-restenosis compounds to produce a formulation for incorporation into drug-eluting stents. Suitable compounds for use in combination with the ApoE analogs disclosed herein include, but are not limited to, paclitaxel, rapamycin (sirolimus), tacrolimus, zotarolimus, everolimus, docetaxel, pimecrolimus, and derivatives thereof.

The ApoE analogs described herein may be used alone to modulate calcineurin activity and promote remyelination or in combination with other standard therapeutic agents prescribed to treat the indicated conditions. In one embodiment, the ApoE analogs may be administered in combination with other immunosuppressants, including sirolimus (rapamycin), other calcineurin inhibitors, glucocorticoids, cytostatics, antibodies, opioids, tumor necrosis factor-alpha binding proteins, such as infliximab (Remicade), etanercept (Embrel), and adalimumab (Humira), and small molecules, such as FTY720. Other calcineurin inhibitors include tacrolimus (FK506), cyclosporin A, and pimecrolimus (Elidel). In another embodiment, the ApoE analogs may be co-administered with other anti-inflammatory agents, such as corticosteroids, hydrocortisone, prednisone and the like as well as anti-inflammatory cytokines, growth factors, or leukocyte migration inhibitory compounds. Useful cytokines include, but are not limited to, IL-4, IL-10, IL-11, and IL-13, particularly IL-4 and IL-10, which are known to suppress production of inflammatory cytokines and to be involved in restoring the immune system. Growth factors include GM-CSF among others. These cytokines and growth factors may be administered as purified proteins—obtained naturally or from recombinant sources—or administered in the form of nucleic acids that express these peptides, particularly as fusion proteins.

The ApoE analogs may also be used in combination with anti-diarrheal agents such as loperamide and the like, anti-bacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, gancyclovir, ribavirin, interferons and the like; analgesic agents such as salicylic acid, acetaminophen, ibuprofen, flurbiprofen, morphine and the like; local anesthetics such as lidocaine, bupivacaine, benzocaine and the like; growth factors such as colony stimulating factor, granulocyte-macrophage colony stimulating factor, and the like; antihistamines such as diphenhydramine, chlorphencramine and the like; anti-nausea medications, nutritional additives such as leukovorin, standard multiple sclerosis therapies, such as beta interferon 1a (Avonex® and Rebif®) and 1b (Betaseron®), glatiramer acetate (Copaxone®), mitoxantrone (Novantrone®), and Tysabri® (Biogen-Idee and Elan), and other like substances. Combination therapies (e.g. ApoE analogs and another therapeutic agent) can be co-administered or formulated together in a single pharmaceutical composition.

The ApoE analogs of the present invention can be administered acutely (i.e., during the onset or shortly after events leading to an inflammatory, neurological, heart, renal, or pulmonary condition), or can be administered prophylactically (e.g., before scheduled surgery, or before the appearance of inflammatory, neurological, cardiac, renal, and/or pulmonary signs or symptoms), or administered during the course of a degenerative disease (e.g. multiple sclerosis) to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

The typical daily regime can be from about 0.01 μg/kg body weight per day, from about 1 mg/kg body weight per day, from about 10 mg/kg body weight per day, from about 100 mg/kg body weight per day, from about 1,000 mg/kg body weight per day. Dosages can be between about 0.01 μg/kg and about 10 mg/kg body weight per day, depending on the ApoE analog, or between about 1 mg/kg and about 10 mg/kg body weight per day.

As used herein, the term "administering to the central nervous system of a subject" refers to the use of routes of administration, as are known in the art, that provide the compound to the central nervous system (CNS) tissues, and in particular the brain and spinal cord, of a subject being treated.

The blood-brain barrier presents a barrier to the passive diffusion of substances from the bloodstream into various regions of the CNS. However, active transport of certain agents is known to occur in either direction across the blood-brain barrier. Substances that can have limited access to the brain from the bloodstream can be injected directly into the cerebrospinal fluid. Cerebral ischemia and inflammation are also known to modify the blood-brain barrier and result in increased access to substances in the bloodstream.

Administration of an ApoE analog directly to the central nervous system is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical agent into the cerebrospinal fluid ("spinal injection") is known in the art, and is suited for administration of the present ApoE analogs.

Pharmacologic-based procedures are also known in the art for circumventing the blood brain barrier, including the conversion of hydrophilic compounds into lipid-soluble drugs. The ApoE analog can be encapsulated in a lipid vesicle or liposome.

The intra-arterial infusion of hypertonic substances to transiently open the blood-brain barrier and allow passage of hydrophilic drugs into the central nervous system is also known in the art. U.S. Pat. No. 5,686,416 to Kozarich et al. discloses the co-administration of receptor mediated permeabilizer (RMP) peptides with compounds to be delivered to the interstitial fluid compartment of the brain, to cause an increase in the permeability of the blood-brain barrier and effect increased delivery of the compounds to the brain.

In particular methods of the invention, it is desirable to administer an ApoE analog to a subject such that the ApoE analog can access cells of the central nervous system. To do so, the ApoE analog is required to cross the blood brain barrier. One method of transporting an active agent across the blood-brain barrier is to couple or conjugate the ApoE analog to a second molecule (a "carrier"), which is a peptide or non-proteinaceous moiety selected for its ability to penetrate the blood-brain barrier and transport the ApoE analog across the blood-brain barrier. In addition to the protein transduction domains described herein, which can facilitate transport across the blood brain barrier, other suitable carriers include pyridinium, fatty acids, lipids, inositol, cholesterol, and glucose derivatives. The carrier can be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 (Pardridge et al). These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198. Specific carrier molecules disclosed include hemoglobin, lysozyme, cytochrome c, ceruloplasmin, calmodulin, ubiquitin and substance P. See also U.S. Pat. No. 5,017,566, which is herein incorporated by reference in its entirety.

The examples which follow are set forth to illustrate the present invention, and are not to be construed as limiting thereof.

EXAMPLES

Example 1

COG Peptides Reduce Spinal Cord Demyelination and Inflammation in a Mouse Model of Multiple Sclerosis A myelin oligodendrocyte glycoprotein (MOG)-induced experimental autoimmune encephalomyelitis (EAE) model of human multiple sclerosis (MS) was used to test whether COG peptides had a therapeutic effect on animals with established disease. C57BL/6J mice were first immunized with MOG to create an EAE model. On the day that an animal first showed a clinical score (CS)≥2, it was randomly assigned to a group treated daily with 1 mg/kg, i.p. of COG 133 (SEQ ID NO: 1), 1 mg/kg, i.p. of COG 112 (SEQ ID NO: 5) or normal saline. Treatment with COG 112 and COG 133 significantly slowed the deleterious progress of the disease and promoted recovery to a normal clinical behavior (FIGS. 1A and B). Even though the peptide treatment started much later (from about day 14 post-immunization (dpi) on average) than that of a pre-treatment paradigm (dpi 2), COG 112 and COG 133 still significantly reduced the maximal severity of disability. The most profound improvement was found with post-treatment of COG 112 where significantly more animals displayed complete recovery or remission from the disease when compared to saline controls. On dpi 35, 71% of COG 112-treated and 50% of COG 133-treated mice exhibited complete remission, however, only 22% of mice in the saline control group completely recovered (FIG. 1B). In addition, both COG 112 and COG 133 significantly reduced the burden of disability as measured by area under curve of FIG. 1A (data not shown).

Figure 2:
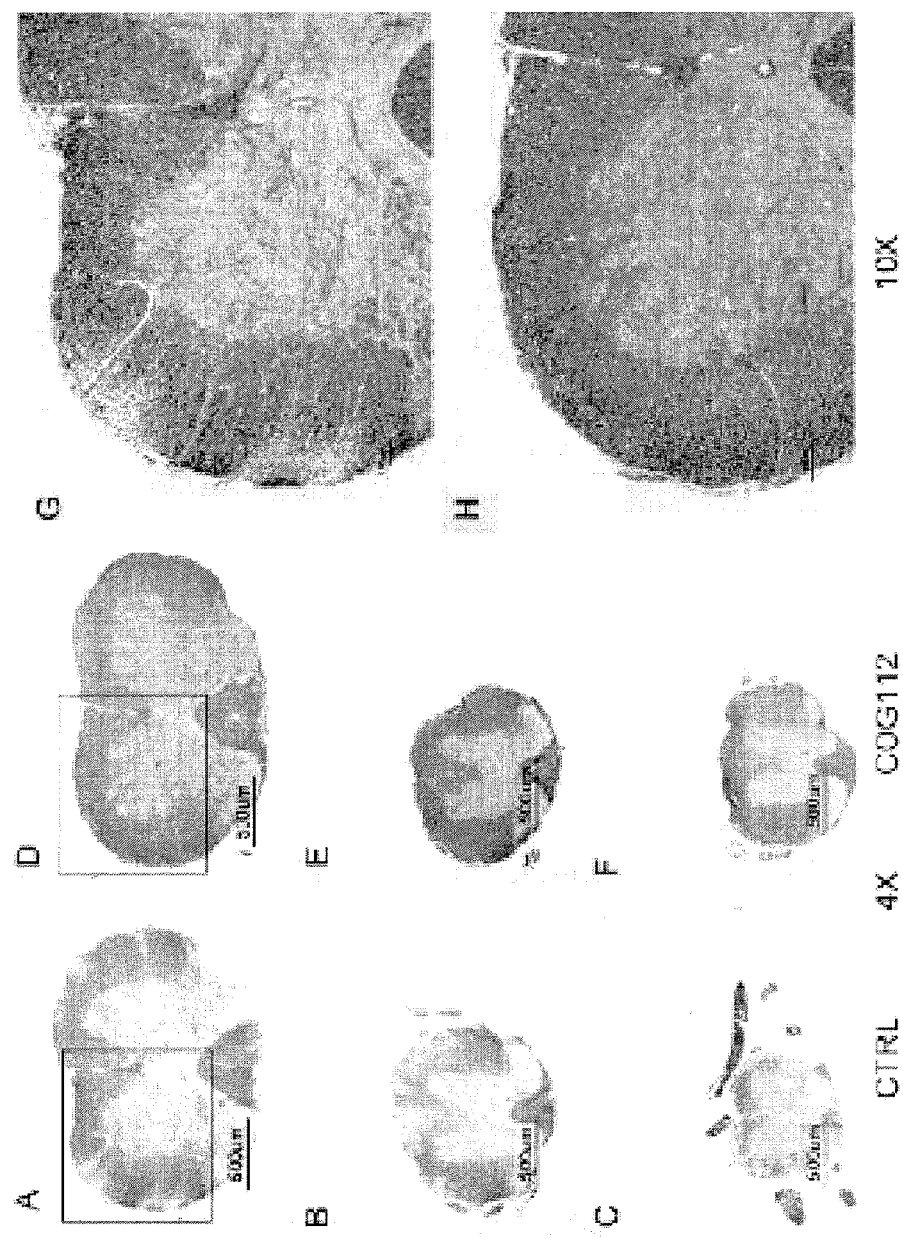
FIG. 2. Representative histopathology of EAE in mice treated with COG 112 or saline control. 5 µm thick sections were stained with Luxol fast blue and eosin to reveal demyelination and peripheral infiltrates. The left panels show the pathological changes in spinal cord from cervical (A), thoracic (B) and lumbar (C) segments of a saline-treated control animal. Demyelination is shown as loss of blue staining in white matter and peripheral infiltrates are stained with purple particles. Panels D, E and F show the corresponding segments of a COG 112-treated animal where no obvious demyelination is observed. The boxed-insets of panel A and D are magnified 10× in panel G and H, respectively.

One of the pathological hallmarks of MS is extensive demyelination of the myelin sheath surrounding neurons accompanied by massive infiltration of peripheral leukocytes into the brain and the spinal cord, all of which contribute to the clinical manifestations of neurological disability. We further examined the effects of COG peptides on demyelination and leukocyte-influx into the spinal cords by Luxol Fast Blue (LFB) and Eosin staining. Saline treated mice displayed severe demyelination (shown as loss of blue staining in white matter) in all segments of the spinal cord as depicted in FIGS. 2A, B, and C, corresponding to the cervical, thoracic and lumbar segments, respectively. Panel G is a magnified view of the boxed area in A. Interestingly, COG 112 and COG 133 treatments greatly reduced demyelination and infiltration of peripheral mononuclear cells in these regions as shown in a representative section from a COG 112-treated mouse in FIGS. 2D, E, F, and H (magnified view of the boxed area in D). These histopathological findings are consistent with the decreased clinical severity of EAE observed in COG 112- and COG 133-treated mice.

Figure 3:
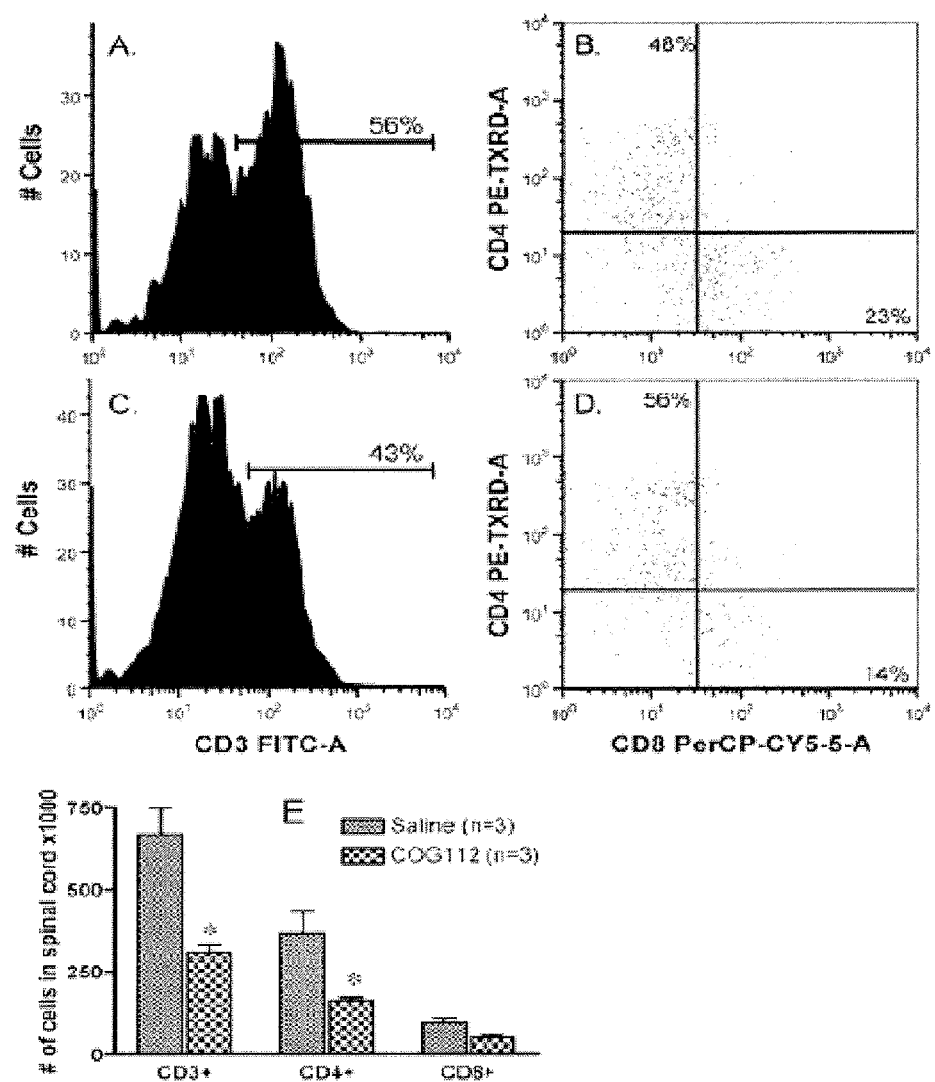
FIG. 3. Profiling and quantification of T cell subset infiltrates in the spinal cords of animals on 21 days post-immunization that were treated with or without COG 112. Single-cell suspensions of spinal cord were stained with anti-CD3, CD4, and CD8 mAbs. Frequency of CD3+CD45+ cytometry (T cell) is represented in control (A) and COG112-treated (C) animals. Frequency of CD4+ and CD8+ T cells is represented in saline control (B) and COG 112-treated (D) mice. Total cell number for each of the specific cell surface markers is calculated and expressed as number per spinal cord (E).

In accord with the histopathological demonstration of inflammatory infiltrates shown above, we also quantified and profiled T lymphocyte infiltrates in the spinal cord to evaluate the effect of COG peptides on T cell migration. Since COG 112 displayed a more potent therapeutic effect than COG 133, we examined the frequency of CD3+, CD4+, and CD8+ T cells in the spinal cords of COG 112-treated mice compared to vehicle controls on dpi 21. Single-cell suspensions of spinal cord were stained with anti-CD3, CD4, and CD8 mAbs. As shown in FIGS. 3A & C, the frequency of CD3+ T cells in the spinal cords of mice treated with COG 112 was reduced as compared to vehicle controls on dpi 21. COG 112 treatment also significantly reduced CD4+ T cell infiltration into the spinal cord (FIG. 3E). However, no significant difference was observed in the number of CD8+ T cells with peptide treatment (Figure B & D).

The results of these experiments show that COG peptides (i.e. ApoE analogs) improve the clinical symptoms of EAE as well as reduce the associated demyelination and inflammation of the spinal cord.

Example 2

COG Peptides Inhibit Macrophage Activation in EAE Mice

Figure 4:
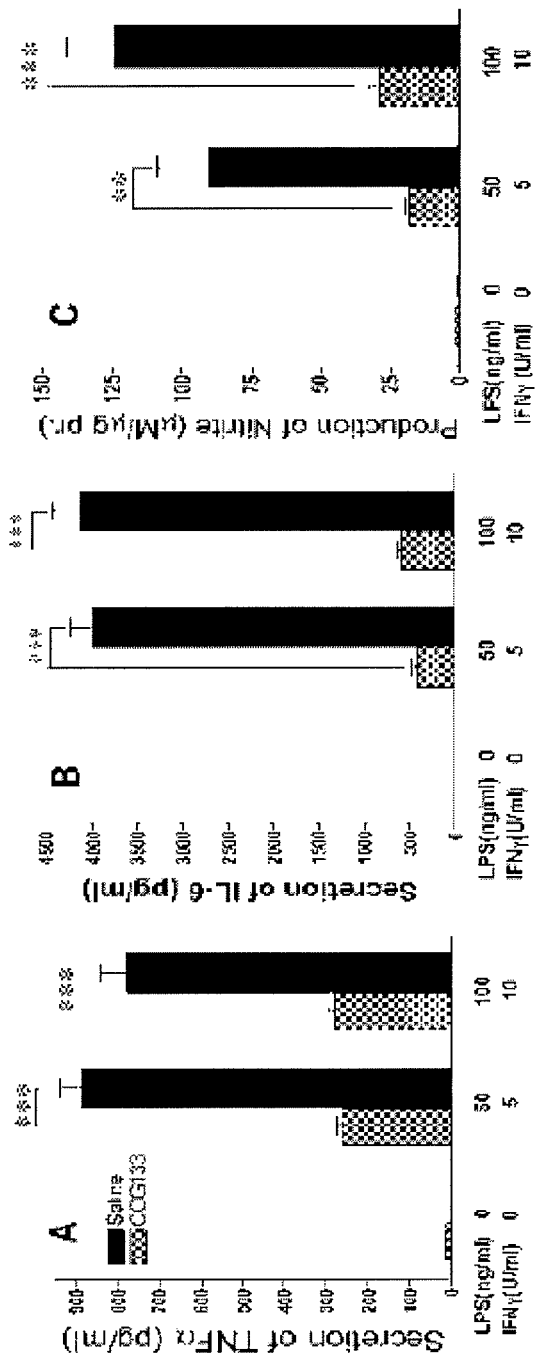
FIG. 4. In vivo exposure to COG 133 suppressed in vitro production of inflammatory effectors by peritoneal macrophages. TNF-α (A) and IL-6 (B) were measured by ELISA, and nitrite in culture medium was measured by a Sievers NO Analyzer (C). Statistical analysis was performed by two-tailed student's t test and significance was shown as  ($p<0.01$) and * ($p<0.001$).

To examine the effect of COG 133 (SEQ ID NO: 1) treatment on activation of macrophages in EAE mice, macrophages were collected from a subset of saline and COG 133-treated mice on dpi 35 and then challenged in vitro with the immune stimulators lipopolysaccharide and interferon-γ (LPS+IFN-γ). Nitrite in culture medium was measured by a Sievers NO Analyzer and TNF-α and IL-6 were measured by ELISA. Upon treatment with LPS and IFN-γ, macrophages derived from saline-treated mice responded with a robust release of TNF-α and IL-6 compared to the significantly lower response of macrophages derived from COG 133-treated mice ($p<0.001$; FIGS. 4A and B). Similarly, macrophages derived from saline-treated mice exhibited a robust release of NO when treated in vitro with LPS+IFN-γ compared to the significantly lower levels of NO released from macrophages derived from COG 133-treated animals ($p<0.001$; FIG. 4C).

Figure 5:
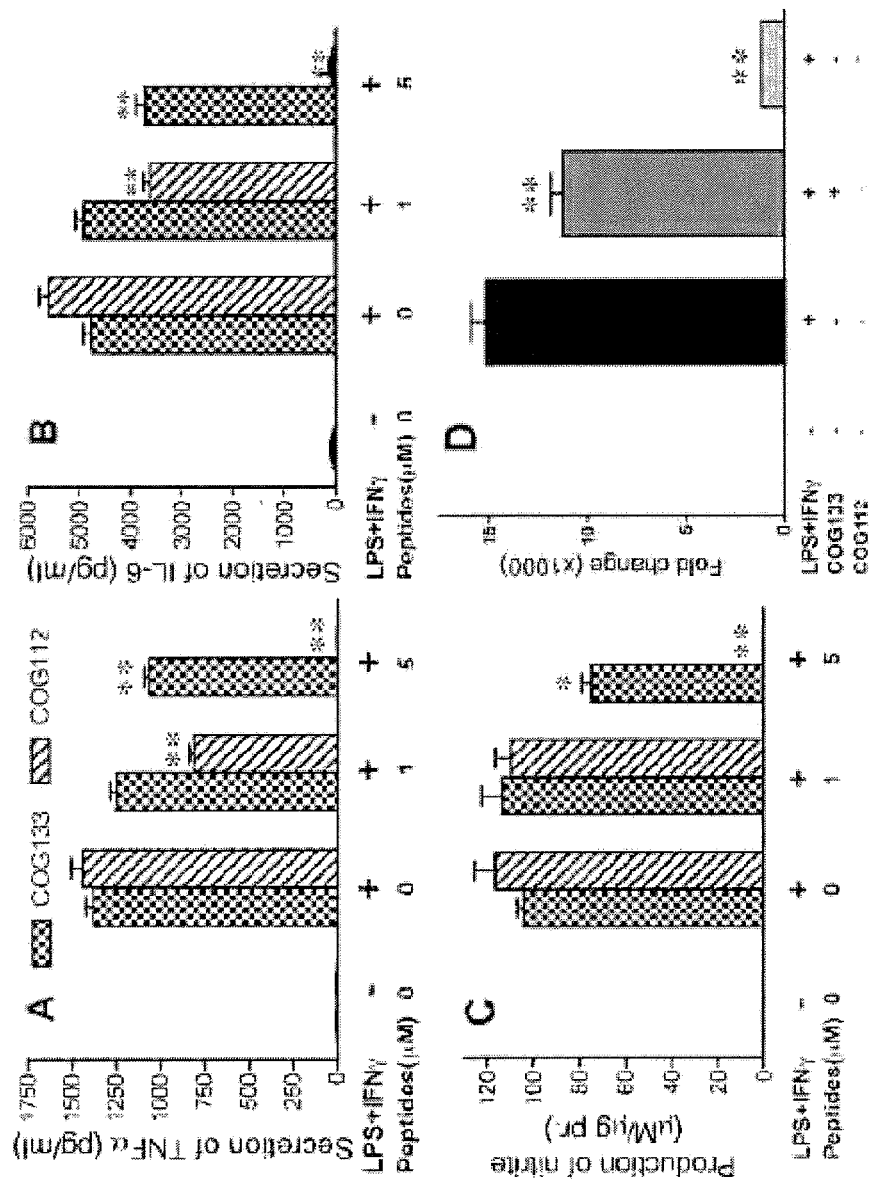
FIG. 5. In vitro effects of COG compounds on LPS and IFN-γ-induced production of inflammatory mediators in cultured peritoneal macrophages isolated from EAE mice. Conditioned medium with or without COG 133 or COG 112 was collected 45 hours after immunogen exposure for analysis of TNF-α (A) and IL-6 (B), or 72 hours after inflammatory stimulation for measurement of nitrite (C). Level of NOS2 expression was assessed by quantitative real-time PCR (D). NOS2 expression was first normalized by the endogenous control (18S rRNA) and then expressed as fold change compared to control group. Statistical analysis was performed by ANOVA and significance was shown as *($p<0.05$) and **($p<0.001$).

We then examined the ability of COG 112 (SEQ ID NO: 5) and COG 133 (SEQ ID NO: 1) to inhibit the in vitro release of NO, TNF-α and IL-6 using macrophages obtained from saline-treated EAE mice on dpi 35. Conditioned medium with or without COG 133 or COG 112 was collected 45 hours after immunogen (LPS+IFN-γ) exposure for analysis of TNF-α and IL-6, or 72 hours after stimulation for measurement of nitrite. COG 112 treatment resulted in a dose-dependent suppression of TNF-α and IL-6 levels, with complete inhibition occurring at about 5 μM (FIGS. 5A and B), while 5 μM of COG 133 exhibited only moderate, yet statistically significant, suppression of both TNF-α and IL-6. In LPS+IFN-γ treated macrophages, 5 μM COG 112 completely inhibited NO release ($p<0.001$ versus control), while the same concentration of COG 133 inhibited NO release by about 37% ($p<0.05$ versus control) (FIG. 5C). Levels of NOS2 expression were quantified by real-time PCR. NOS2 expression was first normalized by the endogenous control (18S rRNA) and then expressed as fold change compared to control group. As shown in FIG. 5D, COG 112 and COG 133 affect NOS2 expression as well as NO production, with COG 112 exhibiting a more potent effect than COG 133.

In summary, macrophage activation in response to stimulation with an immunogen is suppressed by exposure to COG peptides either in vivo or in vitro. Thus, COG peptides are able to modulate the activation status of macrophages, which play a pivotal role in the initiation and progress of inflammatory disease, such as EAE and MS.

Example 3

COG 112 Promotes Remyelination in an in Vivo Model of Demyelination

In an EAE model, treatment with COG 112 reduced demyelination in the spinal cord (Example 1). Therefore, we tested the effect of COG peptides on remyelination in a cuprizone-induced demyelination model. C57BL/6J male mice were fed with 0.2% cuprizone-containing mouse chow for 5 weeks to cause demyelination. At the end of week 5, cuprizone-containing chow was replaced with regular chow and the animals started receiving either vehicle or 1 mg/kg, i.p. COG 112 (SEQ ID NO: 5) three times a week (Monday, Wednesday and Friday paradigm) for 4 weeks. At the end of the treatment period, animals were sacrificed for evaluation of demyelination. 5 μm thick coronal sections containing corpus callosum were stained with Luxol Fast blue (LFB) and eosin. Adjacent sections were labeled with glutathione S-transferase-π (GST-π) antibody to identify mature oligodendrocytes.

Figure 6:
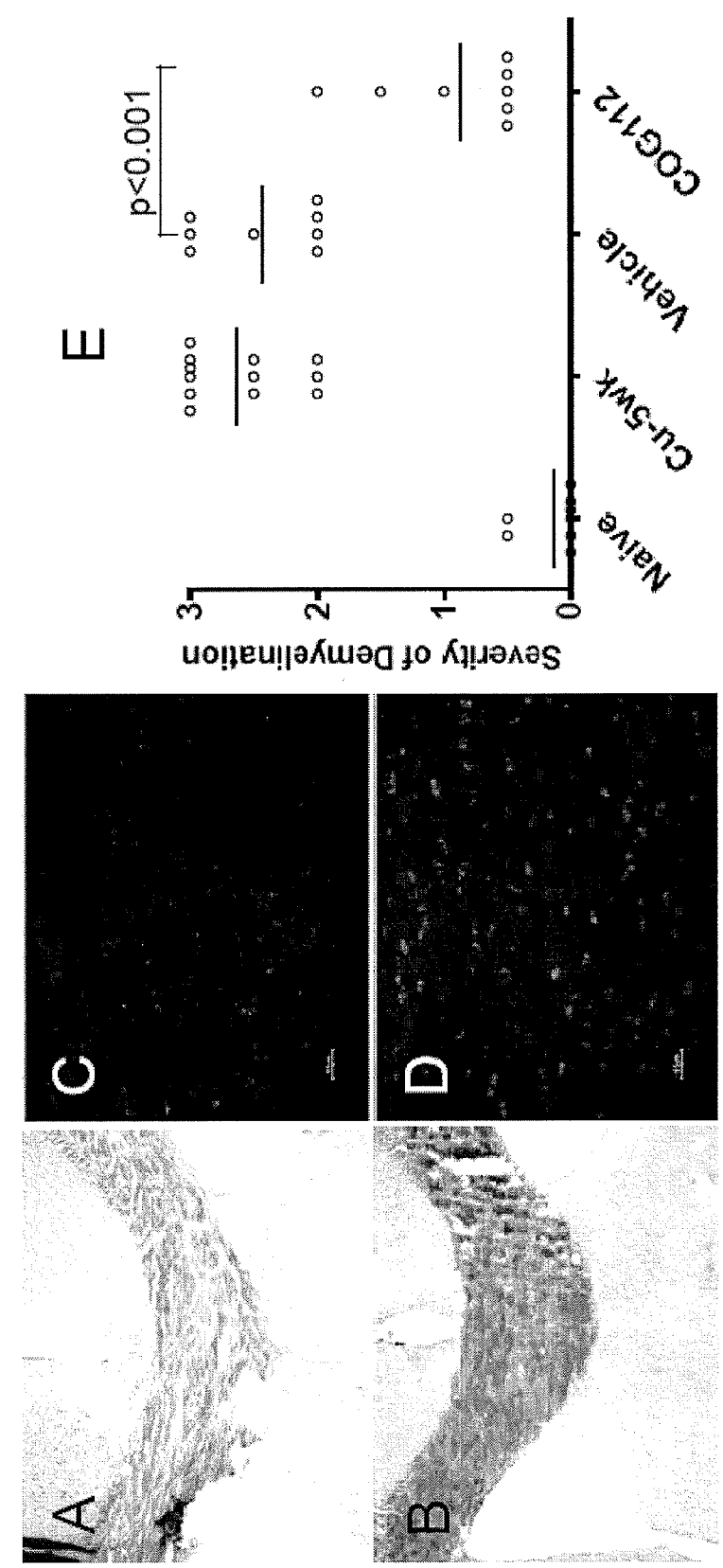
FIG. 6. COG 112 promotes remyelination of the corpus callosum in a cuprizone model of demyelination. C57BL/6J male mice were fed with 0.2% cuprizone-containing diet for 5 weeks to induce complete demyelination in the corpus callosum. Starting from week 6, cuprizone was removed and the animals were treated with either vehicle or COG 112 (1 mg/kg) by i.p. injection three times a week for 4 weeks. Myelination in corpus callosum was evaluated on a scale from 0 to 3 after staining brain sections with Luxol Fast Blue (LFB). The data were collected from 4 animals of each group and 2 sections from each animal. A non-parametric Mann-Whitney test was used to compare differences between groups. Panels A and B (100×) are representative pictures of LFB-stained sections from vehicle- and COG 112-treated animals, respectively. Panels C and D (400×) are representative sections labeled with anti-GST-π-FITC antibody (marker for mature oligodendrocytes) from vehicle- and COG 112-treated animals, respectively.

As shown by the loss of blue staining in the corpus callosum, cuprizone administration for 5 weeks caused extensive demyelination (FIG. 6A). The removal of cuprizone is expected to allow remyelination to occur to some extent. However, no significant remyelination was observed in vehicle-treated animals, in which cuprizone had been absent for 4 weeks (FIG. 6E). In contrast, 1 mg/kg COG 112, administered by i.p. injection three times a week, significantly increased LFB staining of myelin within corpus callosum (FIGS. 6B and E). Given that the treatment was initiated after full demyelination at 5 weeks, these data suggest that COG 112 promotes remyelination. Significantly more GST-π+ cells within the corpus callosum ribbon were observed in COG 112-treated animals compared to vehicle-treated control animals (FIGS. 6C and D). This finding is consistent with the enhanced remyelination within the same area after treatment with COG 112, suggesting COG 112 enhances the migration and/or maturation of oligodendrocyte precursor cells in vivo. Taken together, the results of these experiments suggest that ApoE analogs (i.e. COG peptides) act as remyelinating agents as well as immunomodulatory agents. Thus, ApoE analogs represent a novel therapy for demyelinating disorders.

Example 4

COG 112 Promotes Remyelination in an in Vitro Demyelination Model

Figure 7:
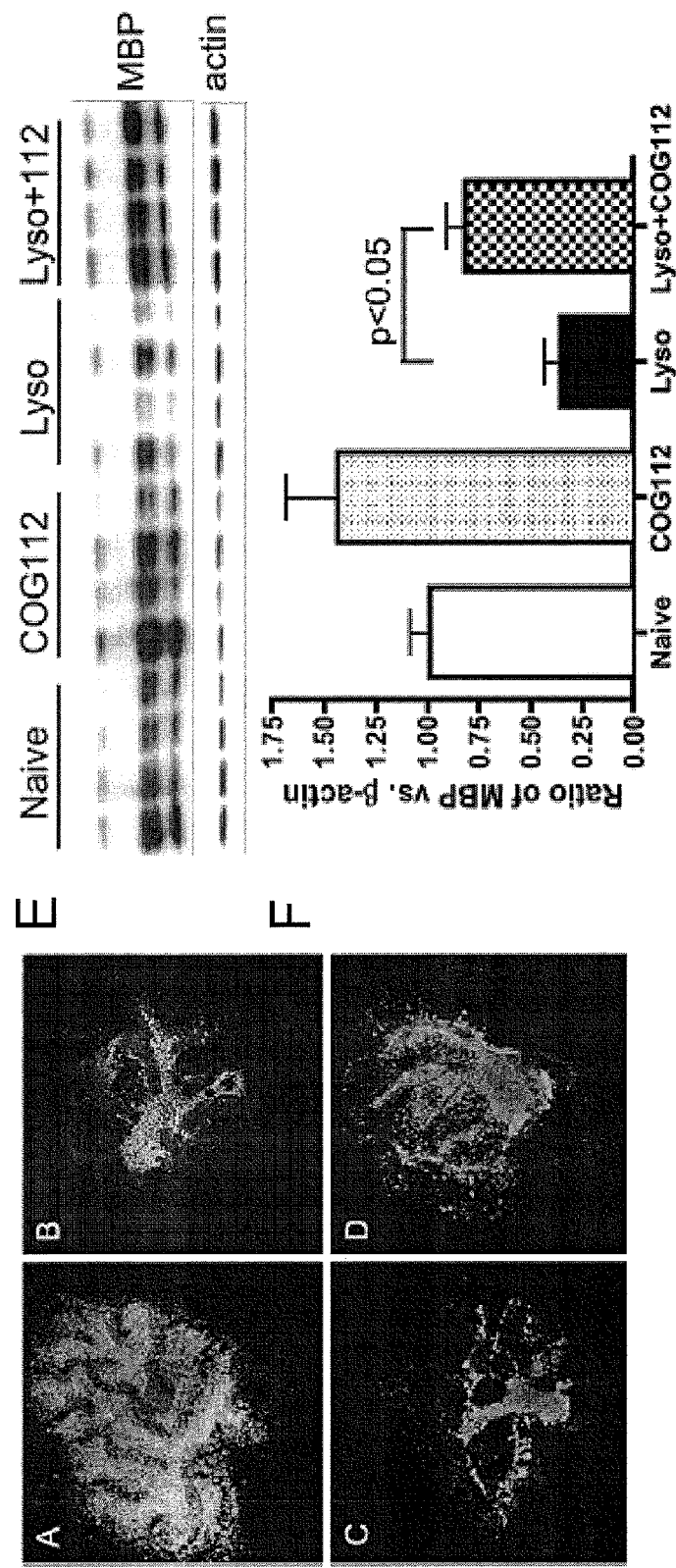
FIG. 7. COG 112 promotes remyelination in a lysolecithin-induced demyelination model in cerebellum slice culture. Cerebellum slices from postnatal day 10 rat pups were cultured for 7 days. Lysolecithin was added to a final concentration of 0.5 mg/ml and then removed after incubation overnight (15~17 hr). 1 µM COG 112 was added to the slice and cultured for 5 days. The cerebellar slices were either immunohistologically stained with MBP; or collected and lysed for western blotting with myelin marker MBP. (A) naïve slice; (B) 2 days after lysolecithin treatment; (C) day 7 after lysolecithin treatment; (D) day 7 after lysolecithin treatment with COG 112 added on day 3; (E) Western blot of cerebellar lysates probed for MBP; (F) Densitometry analysis of blots probed for MBP. The density of each MBP band was normalized to density of β-actin band. One-way ANOVA was used for statistical analysis. n=4

The effect of COG peptides (i.e. ApoE analogs) on remyelination in a second model of demyelination was examined. For this series of experiments, a lysolecithin-induced in vitro demyelination model in an organotypic cerebellar slice culture was used. Parasagittal slices of postnatal Day 10 (P10) rat cerebellum were cut at 400 μm using a Tissue Slicer (SD Instruments, Grants Pass, Oreg.). After culture in conditioned medium for 7 days in vitro (DIV), fresh medium with lysolecithin (0.5 mg/ml) was added to the slice and incubated overnight (15-17 hours) at 37° C. The lysolecithin-containing medium was then replaced with fresh medium without lysolecithin. On day 3, COG 112 (1 μM) was added to the slice with fresh medium. After incubation for 5 days, the cerebellar slices were either immunohistologically stained for myelin basic protein (MBP), a myelin marker, (FIG. 7A-D) or lysed for western blotting and subsequent probing for MBP (FIGS. 7E and F). The glial specific toxin, lysolecithin, induced significant demyelination 5 days later (FIG. 7C), while post-treatment with COG 112 robustly elevated the level of MBP protein (FIG. 7D), suggesting COG 112 treatment enhanced remyelination. Similar results were obtained from the Western blot analysis of lysates of the cerebellar slices (FIGS. 7E and F). Lysolecithin-treated slices exhibited a reduced level of MBP, while post-treatment with COG 112 increased MBP levels. In addition, the blots of cerebellar slice lysate were also probed for oligodendrocyte (OL) marker 2',3'-Cyclic Nucleotide 3'-Phosphodiesterase (CNPase). COG 112 significantly increased the level of CNPase (data not shown), suggesting that COG 112 increased the number of OLs. Because COG 112 was added after demyelination was established, the increased number of OLs is likely to be the result of maturation of oligodendrocyte precursor cells (OPCs).

Figure 8:
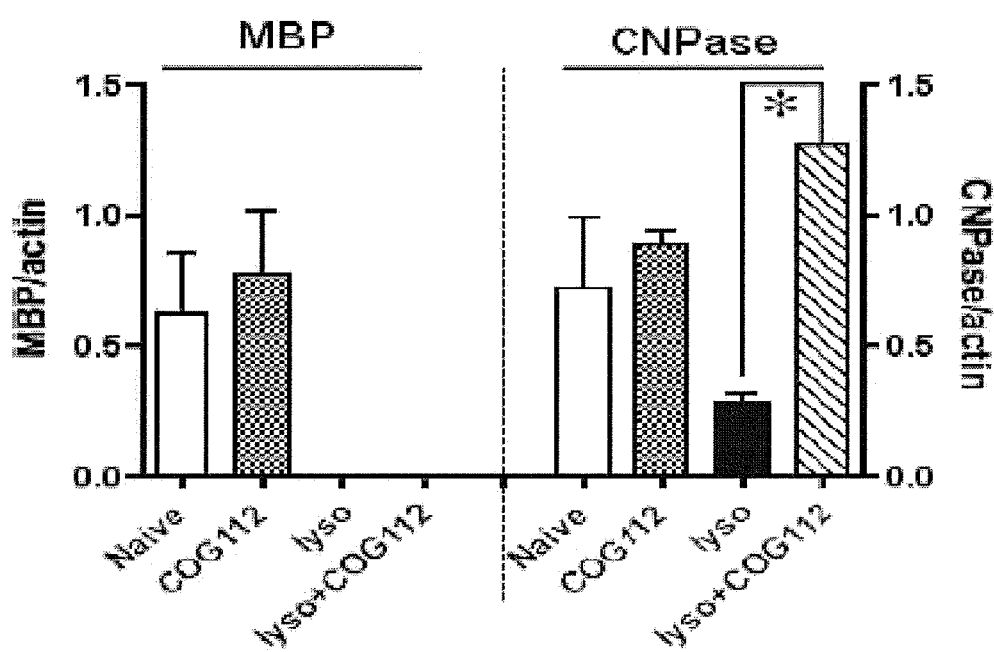
FIG. 8. COG 112 prevents lysolecithin-induced cell death of oligodendrocytes in cerebellum slice culture. Cerebellum slices from postnatal day 10 rat pups were cultured for 7 days. Lysolecithin was added to a final concentration of 0.5 mg/ml with and without COG 112 (1 µM). After incubation overnight (16 hr), medium was replaced with fresh lysolecithin-free medium, but still containing COG 112 for the COG 112 treatment group. After two days, the cerebellar slices were collected and lysed for western blotting with myelin marker MBP (left panel) and oligodendrocyte marker CNPase (right panel). The density of each MBP or CNPase band was normalized to the density of the β-actin band. One-way ANOVA was used for statistical analysis. n=4, * $p<0.01$.

We next investigated whether COG 112 could prevent lysolecithin-induced demyelination. Cerebellar slices from postnatal day 10 rat pups were cultured for 7 days. Lysolecithin was added to a final concentration of 0.5 mg/ml in the presence or absence of COG 112 (1 μM). After incubation overnight (16 hours), medium was replaced with fresh lysolecithin-free medium, but the medium in the COG 112-treatment group still contained COG 112. After 2 days, the cerebellar slices were collected and lysed for western blotting with myelin marker MBP and oligodendrocyte marker CNPase. The density of each MBP or CNPase band was normalized to the density of the β-actin band. As shown in FIG. 8, COG 112 did not prevent lysolecithin-induced demyelination (left panel), but did prevent oligodendrocyte cell death as evidenced by the higher level of CNPase in the COG 112-treated group (right panel).

Example 5

COG Peptides Enhance the Survival and Proliferation of Oligodendrocyte Precursor Cells A shortage of oligodendrocyte precursor cells/oligodendrocytes (OPCs/OLs) in the locus of demyelination could be responsible for the failure to remyelinate. The insufficient number of OPCs may be largely due to progressive cell death by repeated or chronic autoimmune insults. It is known that OPCs are very vulnerable to the inflammatory microenvironment during the autoimmune attack, which is mostly dependent on microglia activation (Lehnardt et al. (2002) J Neurosci., Vol. 22(7):2478-2486). Therefore, inhibition of microglia activation and subsequent inflammatory factors may preserve the OPCs and benefit subsequent remyelination by surviving oligodendrocytes.

Figure 9:
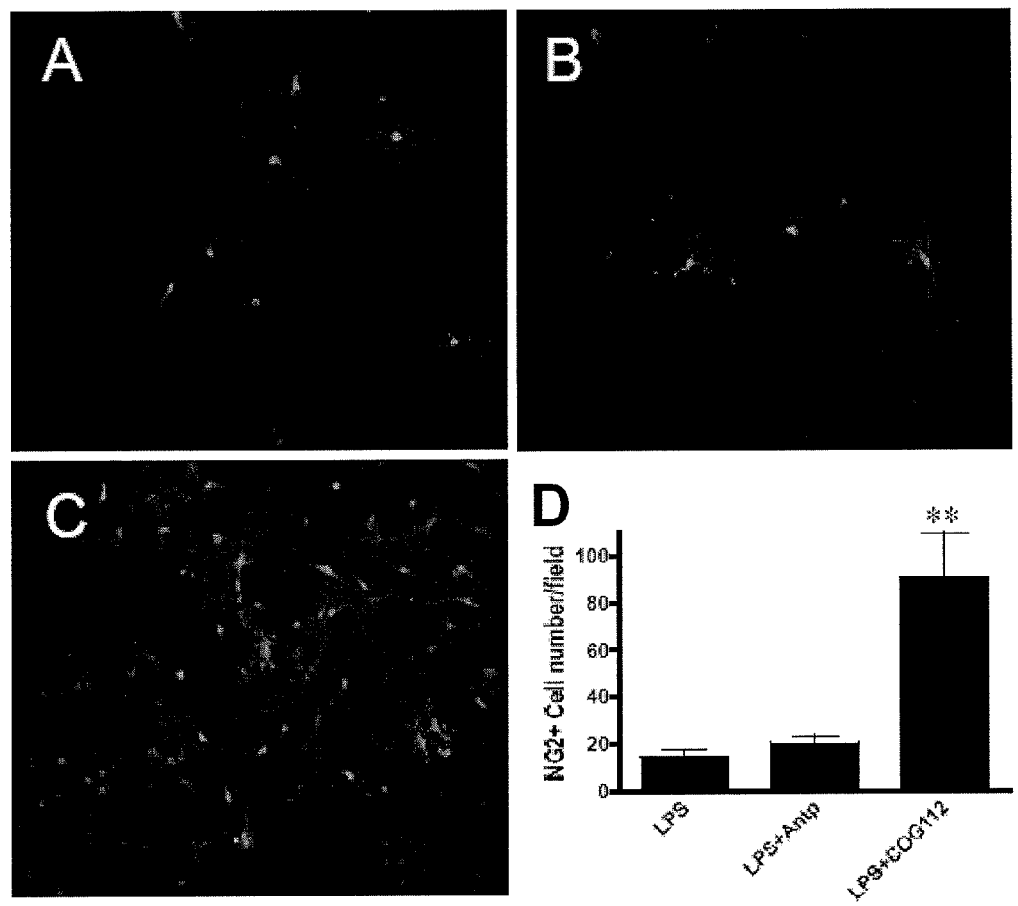
FIG. 9. COG 112 protects OPCs from LPS-induced cell death in OPC/microglia mixed culture. LPS (final conc. 10 ng/ml) was added to an OPC/microglia mixed culture with or without 1 µM COG 112. The prefix peptide of COG 112, antennapedia, was used as a negative control. Cells were fixed with 4% formaldehyde and stained with the OPC marker, NG2, and counterstained with hoescht. (A) LPS-treated cultures; (B) LPS+antennapedia (Antp)-treated cultures; (C) LPS+COG 112-treated cultures; (D) Bar graph summarizing the number of NG2+ cells per field in each condition. ** p<0.01.

Given that COG peptides can robustly inhibit microglia and macrophage activation (Li et al. (2006) J Pharmacol Exp Ther., Vol. 318(3):956-965), we tested whether COG 112 could protect OPCs from inflammation-mediated cell death in an OPC-microglia mixed culture. A primary culture prepared from the brains of P2 Sprague-Dawley rat pups was grown for seven days. Microglia and OPCs were shaken off from the primary culture with an orbital shaker at 150~200 rpm. The OPCs and microglia were plated in 24-well plates at a 1:1 ratio with $5 \times 10^4$ cells per well of each cell type. After 24 hours, LPS (final conc. 10 ng/ml) was added with or without 1 μM COG 112. The prefix peptide of COG 112, antennapedia, was used as a negative control. After incubation for 72 hours, the medium was removed and cells were fixed with 4% formaldehyde and stained with the OPC marker, NG2, and counterstained with hoescht. Five fields from each of the wells were randomly chosen to count the number of NG2-positive cells. As shown in FIG. 9, COG 112 significantly reduced LPS-induced cell death of OPCs, while its prefix peptide (antennapedia) did not have any effect.

Figure 10:
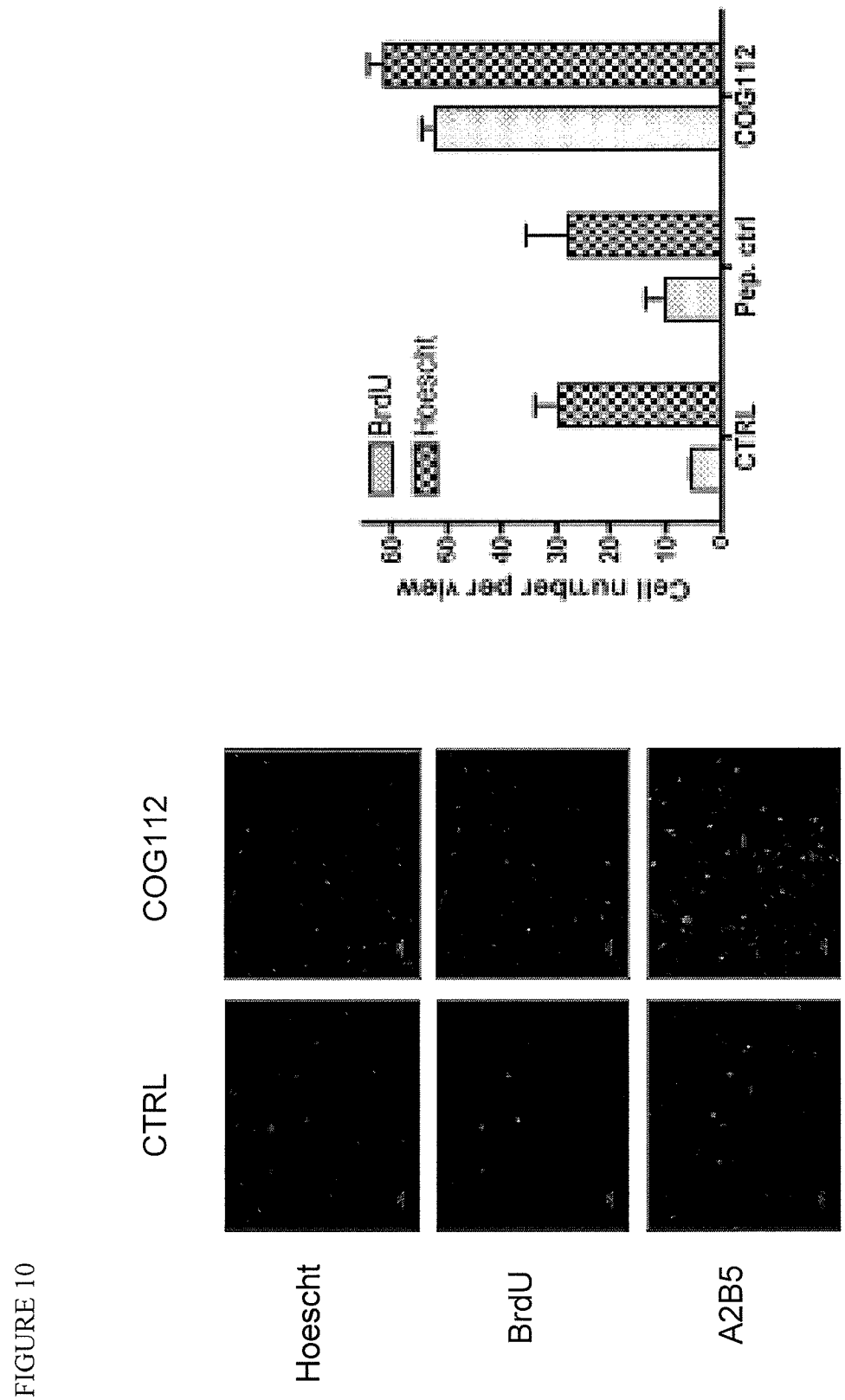
FIG. 10. ApoE analog promotes proliferation of OPCs in culture. Cultures enriched in OPCs were grown in proliferation media containing BrdU in the presence and absence of 1 μM COG 112 or a peptide control. Cells were subsequently labeled with Hoescht stain to detect nuclei, a BrdU antibody to detect proliferating cells, and an A2B5 antibody to identify OPCs (left panel). The number of cells per field were counted for each condition (right panel). In graph, the Hoescht bars correspond to the total number of $A2B5^+/Hoescht^+$ cells, while the BrdU bars correspond to $A2B5^-/BrdU^+$ cells.

We next determined whether ApoE analogs (e.g. COG peptides) had an effect on OPC proliferation in addition to their ability to enhance OPC survival. Enriched OPCs were collected by shaking a primary culture of P2 rat pup brain. Proliferation medium containing COG 112 (1 μM), BrdU (20 μM), 10 ng/mL FGF and PDGF was added to the enriched OPC cultures. After three days in culture, cells were stained with Hoescht stain to show nuclei, a BrdU antibody to identify proliferating cells, and an A2B5 antibody to identify OPCs (FIG. 10). Antennapedia, the prefix peptide of COG 112, was used as a control. COG 112 significantly increased the number of A2B5$^+$/BrdU$^+$ cells, suggesting that ApoE analogs promote OPC proliferation (FIG. 10, right panel).

Figure 11:
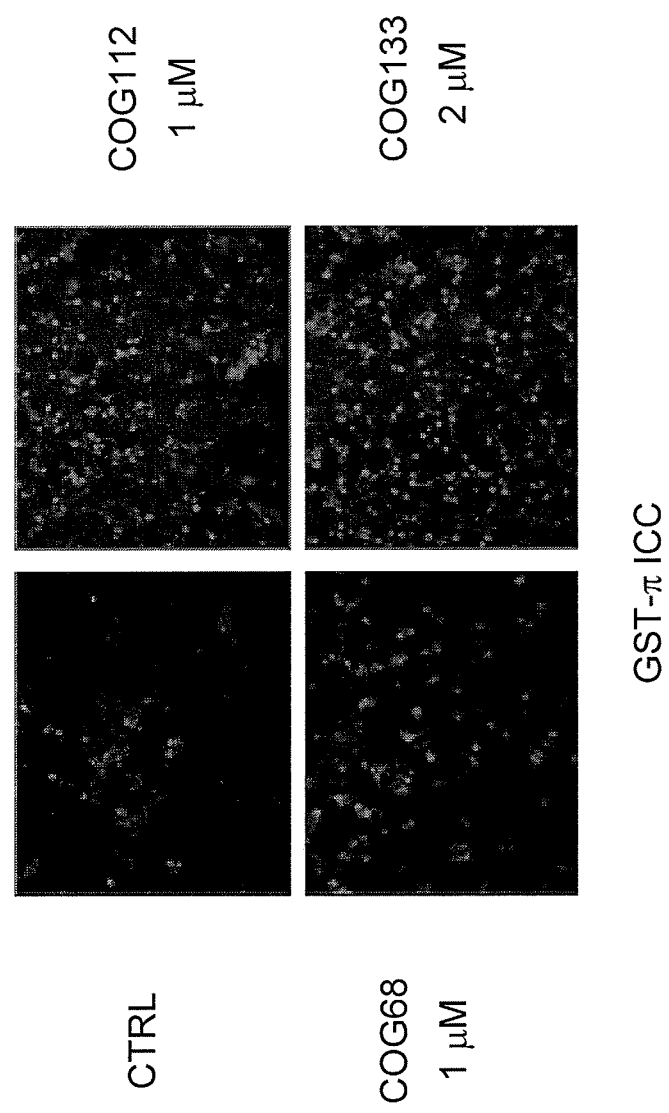
FIG. 11. ApoE analogs increase the number of mature oligodendrocytes in culture. ApoE analogs (COG 133, COG 112, and COG 68) were added to enriched OPC culture in proliferation media for four days. Cultures were then differentiated in the absence of the ApoE analogs. Cells were labeled with a GST-π antibody to detect mature oligodendrocytes.

Since COG 112 increased the proliferation of OPCs, we next examined whether the ApoE analogs could also increase the number of mature oligodendrocytes. Enriched OPC cultures were prepared as described for the previous experiment. 2 µM COG 133 (SEQ ID NO: 1), 1 µM COG 112 (SEQ ID NO: 5), or 1 µM COG 68 (Ac-RRLSYSRRRFLRVRLASHL-RKLRKRLL-NH2; SEQ ID NO: 7) were added to the enriched OPC cultures in proliferation media for four days. The media was then replaced with differentiation medium without the ApoE analogs for an additional six days. Cells were labeled with a GST-π antibody to detect mature oligodendrocytes. All three ApoE analogs significantly increased the number of mature oligodendrocytes in culture (FIG. 11).

The findings of this series of experiments demonstrate that ApoE analogs enhance the proliferation of OPCs as well as their survival in an inflammatory environment. ApoE analogs also increase the number of mature oligodendrocytes (OLs). The ability of ApoE analogs to preserve the number of OPCs/OLs and their function may be one mechanism by which ApoE analogs promote remyelination.

Example 6

Effect of COG Peptides on Spinal Cord Injury

Figure 12:
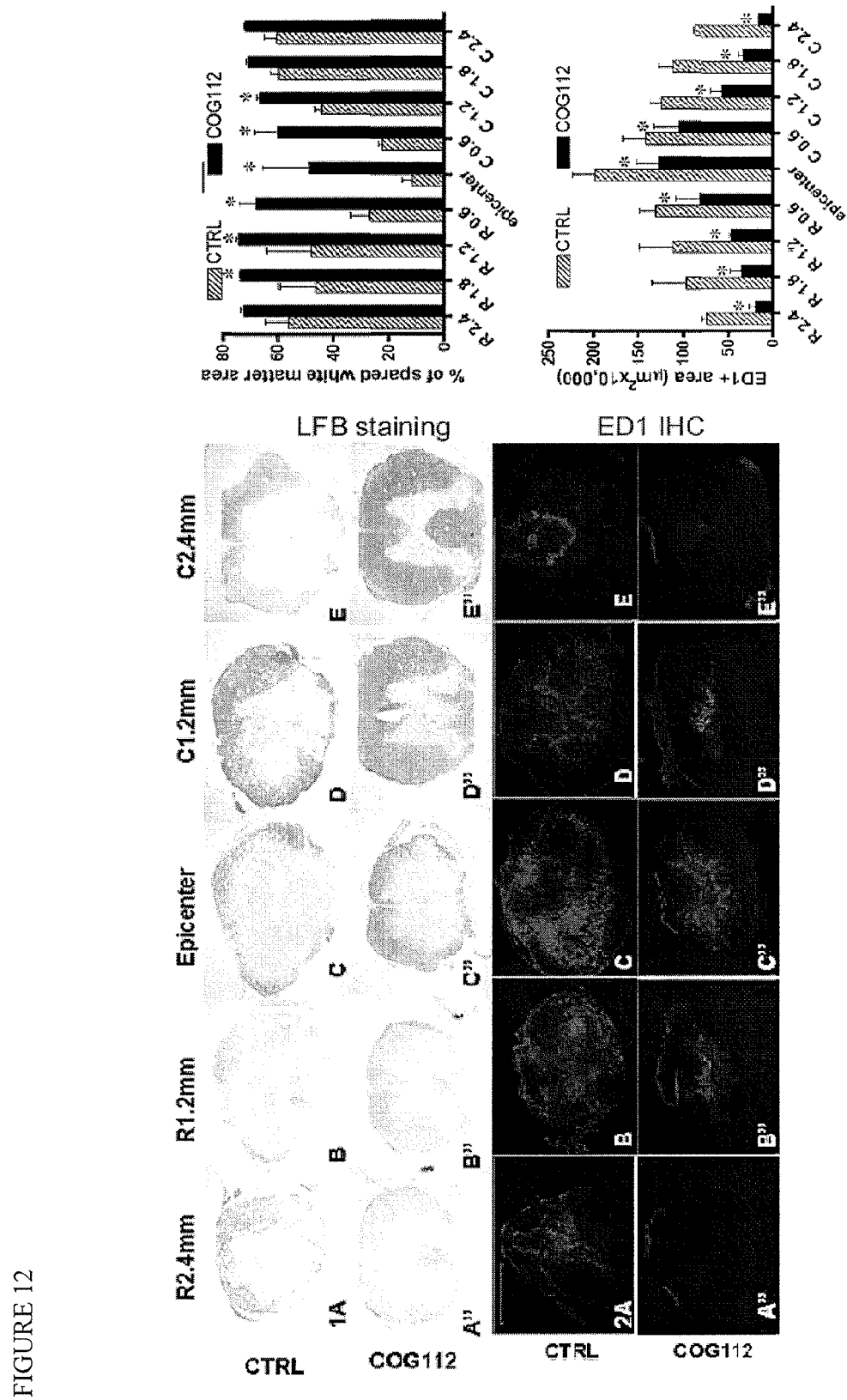
FIG. 12. COG 112 reduces the size of the lesion in white matter after spinal cord injury by inhibition of microglia activation. Rats received 175 kdyn contusive spinal cord injury and subsequent treatment with saline or COG 112 starting immediately after injury for 1 week. The injured area and spared white matter from the injured spinal cord were evaluated and quantified by luxol fast blue (LFB) staining area (top left panel). Activation of microglia was examined by staining adjacent sections with an ED1 antibody (bottom left panel). Compared to animals treated with saline (A-E), the lesion was significantly decreased in COG 112-treated animals (A"-E"). The percentage of spared white matter area to the total spinal cord was significantly increased in the COG 112-treated group (top right panel). COG 112 dramatically suppressed the activation of microglia after injury as shown by the significant decrease in area of ED1 immunoreactivity in the injured spinal cord (bottom right panel). Scale bar=1000 μm.

Similar to MS, spinal cord injury (SCI) is another devastating neurological disorder manifested as massive demyelination in the white matter of the spinal cord and extensive microglial activation surrounding the injured site. To examine the therapeutic effect of ApoE analogs on spinal cord injury, COG 112 (SEQ ID NO: 5) was administered to rats immediately after a contusive spinal cord injury. Female Sprague-Dawley rats were subjected to 175 kdyn contusive impact with the Infinite Horizon Spinal Cord Impactor (Infinite Horizon, L.L.C., Lexington, Ky.) at the T9 level of the exposed spinal cord Immediately after injury, the animal received the first dose of COG 112 (1 mg/kg) or vehicle by tail vein injection. The second dose of COG 112 or vehicle was given i.v. 5 hours later followed by daily i.p. doses for 7 days. The animals were sacrificed on day 7 and the spinal cord spanning the injured site was subjected to histological examination. The injured area and spared white matter of the spinal cord were evaluated by Luxol Fast blue (LFB) staining. Activation of microglia was examined by staining adjacent sections with an antibody to ED1. The percentage of spared white matter (WM) to total spinal cord area at epicenter, 0.6 mm, 1.2 mm, 1.8 mm or 2.4 mm rostral (R) or caudal (C) from epicenter was significantly higher in COG 112-treated animals than animals treated with saline (FIG. 12, top panels). These results show that COG 112 significantly reduced the size of the lesion and preserved the white matter from contusive injury to the spinal cord. Most impressively, about 50% of spared tissue remained at the epicenter of COG 112-treated animals, while only 15% remained in control animals. Similar protection was also observed with COG 112 in a compression model of spinal cord injury in mice (data not shown).

The microglia surrounding the injured spinal cord were robustly activated as shown by ED1-immunoreactivity 7 days after contusion (FIG. 12, bottom panels). Treatment with COG 112 dramatically decreased the ED1 immunoreactive area in the injured spinal cord. Decrease of ED1+ area in caudal or rostral spinal cord was more obvious than in the injured epicenter (FIG. 12, bottom right panel), suggesting that COG 112 suppresses the activation of microglia and the inflammatory reaction after spinal cord injury.

Taken together, these findings support the use of ApoE analogs for treatment of spinal cord injury as well as other demyelinating disorders. ApoE analogs would prevent inflammation-mediated demyelination thus preserving nerve tissue, which would benefit functional recovery.

Example 7

COG 112 Promotes the Functional Recovery from Sciatic Nerve Injury

Figure 13:
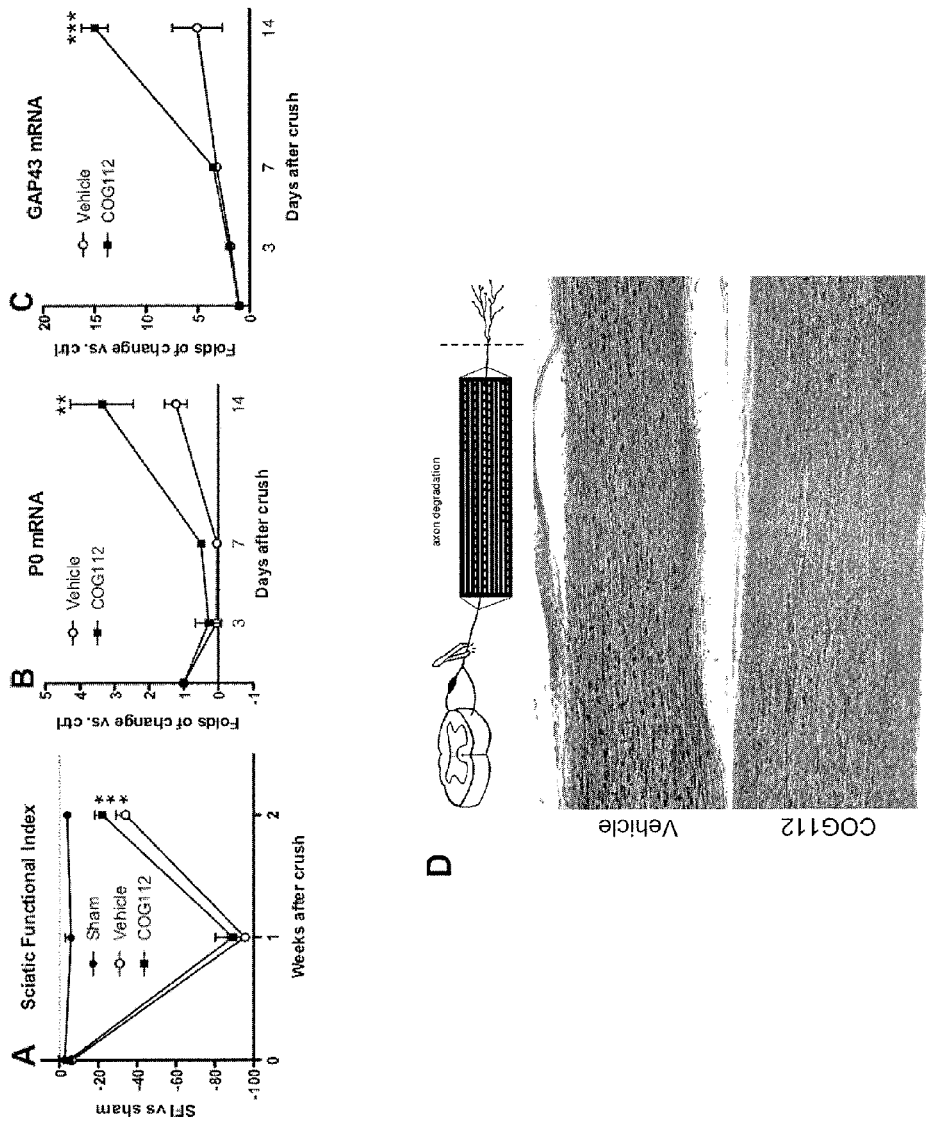
FIG. 13. COG 112 attenuates axonal neurodegeneration and promotes functional recovery after sciatic nerve crush. C57BL mice were subjected to sciatic nerve crush on left hindlimb using a number 5 jeweler's forceps. The animals received lactated Ringer's buffer or COG 112 (1 mg/kg) by i.p. 2 hr after crush followed by daily dose for 14 days. (A) To assess functional deficits after nerve crush, footprints were recorded and the Sciatic Functional Index (SFI) was calculated. COG 112 treatment for 14 days significantly improved functional recovery. * P<0.001. Treatment with COG 112 also robustly augmented the mRNA expression of peripheral myelin marker P0 (B) and axonal regeneration marker GAP43 (C) quantified by real-time PCR. P<0.01; P<0.001. (D) On day 4 after injury, the sciatic nerves were dissected and stained with FD NeuroSilver kit to reveal degenerating axons manifested as dotted lines as depicted in the schematic above the micrographs.

We used a sciatic nerve crush model to investigate whether ApoE analogs can prevent functional loss and/or promote functional recovery after nerve injury. C57BL/6J male mice were anesthetized and the sciatic nerve on left hindlimb was crushed with Number 5 Jeweler's forceps at mid-thigh level for 30 seconds. The animals were then randomly assigned to receive either COG 112 (1 mg/kg, i.p.) or lactated Ringer's buffer two hours after crush followed by daily dose for 14 days. On day 4, two animals from each group were sacrificed and crushed sciatic nerves were dissected and silver stained using a FD NeuroSilver® staining kit to reveal degenerating axons. As shown in FIG. 13D, treatment with COG 112 significantly reduced axonal degeneration, indicating that COG 112 could protect nerves from degenerative damage after injury.

On day 7 and 14, footprints for each animal were taken for quantitative assessment of hindlimb motor function. A Sciatic Functional Index (SFI), which takes into account the relationship between toes and feet of an animal's hindlimb, was calculated for each animal as previously described (Bain et al. (1989) Plast. Reconstr. Surg., Vol. 83(1):129-38). SFI values of zero and 100 indicate normal and complete dysfunction, respectively. As shown in FIG. 13A, animals developed serious hindlimb dysfunction one week after sciatic nerve crush. Administration of COG 112 significantly improved functional recovery after treatment for 2 weeks compared to the vehicle control group (P<0.001).

In order to examine the effect of COG 112 on remyelination and regeneration of axons, segments of sciatic nerves spanning the crushed sites were dissected and collected on day 3, 7 and 14 for examination of P0, a marker of peripheral myelination, and growth associated protein 43 (GAP43), a marker of axonal regeneration, mRNA by real time PCR. COG 112 robustly increased the expression of both P0 (FIG. 13B) and GAP43 (FIG. 13C) after treatment for 2 weeks. These data collectively suggest that COG compounds can promote functional recovery by inhibiting Wallerian degeneration after sciatic nerve crush and promoting axonal remyelination and regeneration.

Example 8

ApoE Analogs Inhibit Calcineurin Activity

Calcineurin (also referred to as protein phosphatase 2B or PP2B) is a calcium-dependent serine/threonine phosphatase that is activated in response to inflammatory stimuli. Calcineurin can dephosphorylate a number of targets, such as the NFAT family of transcription factors, that lead to the expression of proteins involved in the immune response. To further elucidate the mechanism by which ApoE analogs inhibit inflammation-induced demyelination, the effect of COG peptides on calcineurin activity was examined.

Figure 14:
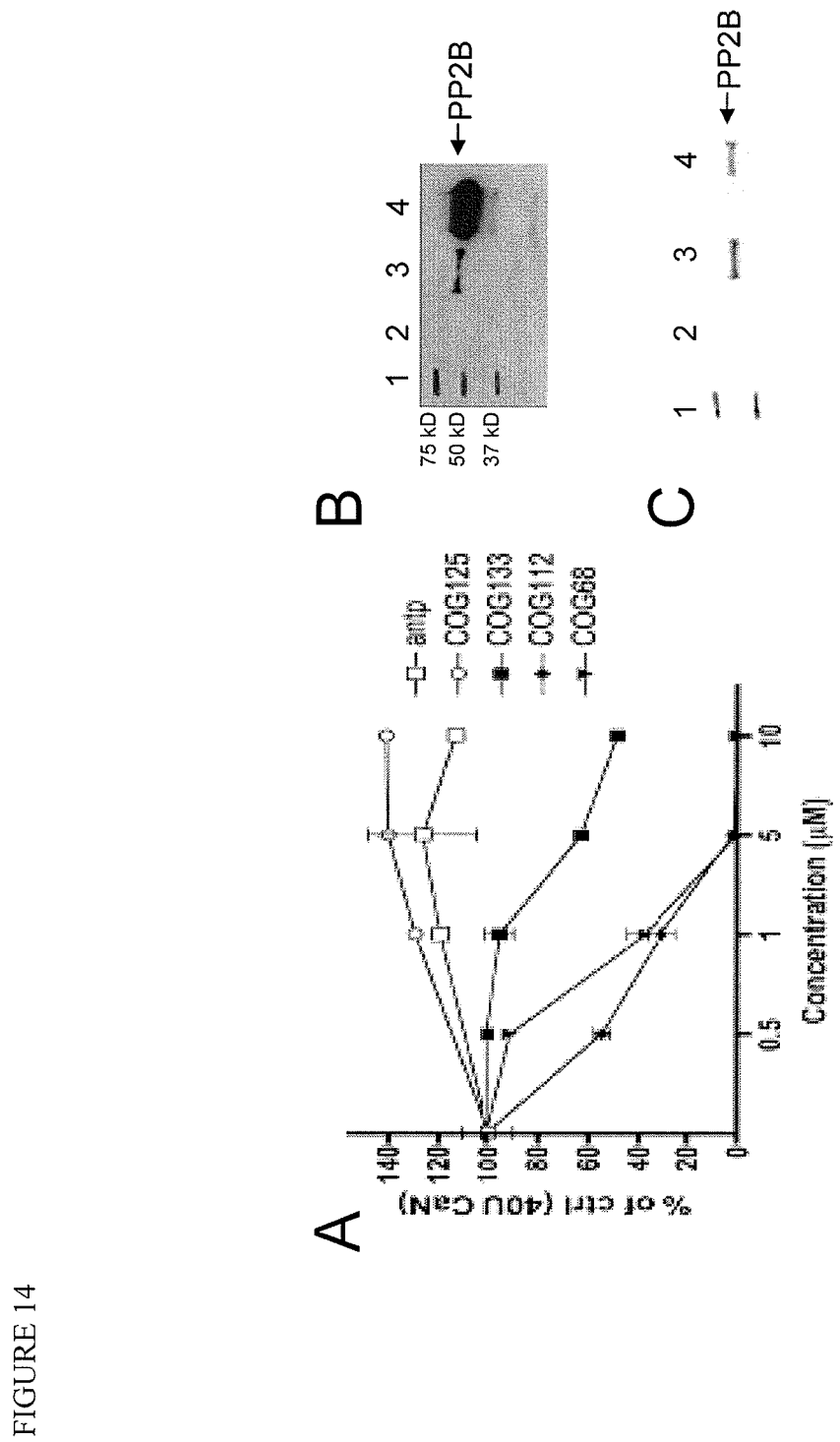
FIG. 14. ApoE analogs bind directly to calcineurin and inhibit its activity. (A) Dose-dependent inhibition of calcineurin activity by different ApoE analogs. Inactive peptide COG 125 and antennapedia (antp) were used as negative controls. (B) Immunoprecipitation of human brain lysate with a biotin-COG 133 conjugate. Lane 1=markers; lane 2=clear bead; lane 3=biotin-COG 133 bead conjugate; and lane 4=10 μg lysate. (C) Immunoprecipitation of different glial cultures with a biotin-COG 133 conjugate. Lane 1=markers; lane 2=astrocyte; lane 3=microglia; and lane 4=oligodendrocyte precursor cells (OPC). Blots in B and C were probed for calcineurin (PP2B).

Calcineurin activity was measured in a cell-free in vitro assay in the presence of various concentrations of COG 133 (SEQ ID NO: 1), COG 112 (SEQ ID NO: 5), COG 68 (SEQ ID NO: 7), COG 125 (Ac-AS(Aib)LRKL(Aib)KR—COOH; SEQ ID NO: 8), or antennapedia (antp), the prefix peptide for COG 112. Inactive COG 125 peptide and antennapedia were used as negative controls. Using a BioMol Calcineurin Phosphatase Activity Kit (Cat. #AK-804), the assay was conducted according to manufacturer's instructions. All three active COG peptides produced a dose-dependent inhibition of calcineurin activity (FIG. 14A). This inhibition of calcineurin activity by ApoE analogs is mediated by a direct interaction of the ApoE analog with the phosphatase. As shown in FIGS. 14B and C, immunoprecipitates from human brain or primary culture revealed that calcineurin (PP2B) bound to COG 133.

Figure 15:
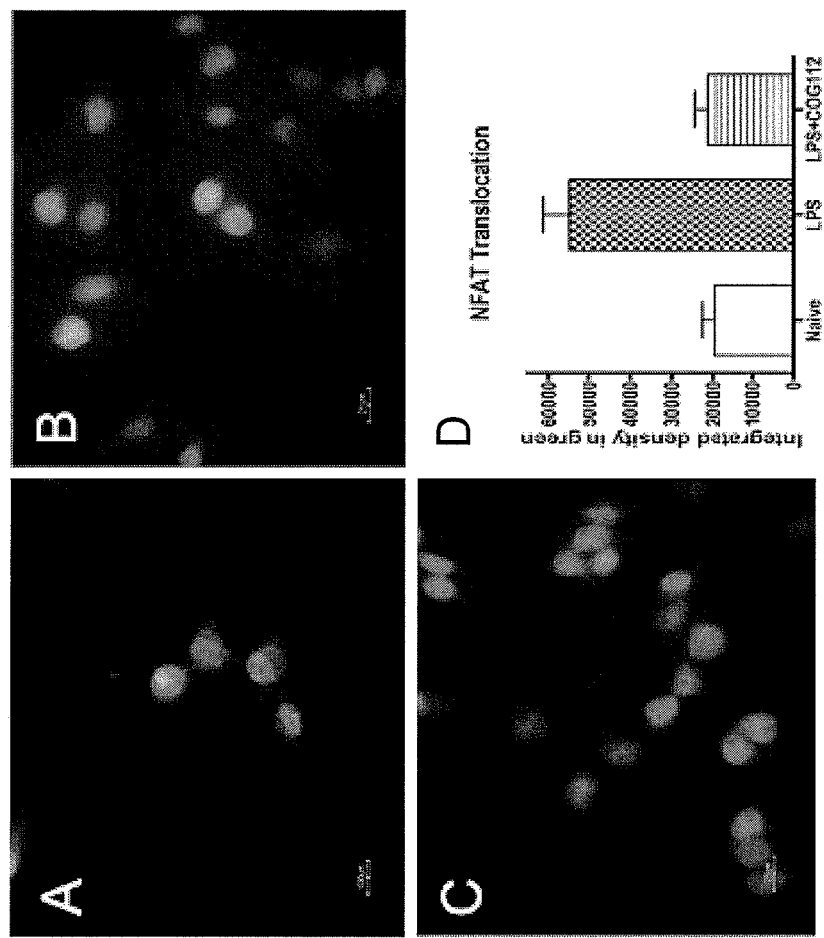
FIG. 15. ApoE analog inhibits LPS-induced NFAT translocation. Murine microglial cell line, BV2 cells were stimulated with LPS in the presence or absence of COG 112. NFAT (green signal) and nuclear label (red signal). (A) Untreated cultures; (B) LPS-treated cultures; (C) LPS+COG 112-treated cultures; (D) NFAT translocation was quantified by the fluorescence intensity of green fluorescence in the nucleus defined by yellow area.

Calcineurin dephosphorylates the transcription factor NFAT, which leads to its activation and translocation to the nucleus. Activation of calcineurin and subsequent activation of NFAT is induced by inflammatory stimuli. To further examine the effect of ApoE analogs on calcineurin signaling, murine microglial cell line, BV2 cells were stimulated with LPS (10 ng/mL) in the absence and presence of COG 112 (2 μM). After incubation for 15 min at 37° C., the cells were washed and fixed with 4% formaldehyde. After staining with 1/100 anti-NFAT antibody coupled with Alexaflour and then counterstained with hoescht nuclear dye, NFAT translocation was quantified by the fluorescence intensity of Alexaflour in the nucleus. As shown in FIG. 15, COG 112 prevented NFAT translocation in response to stimulation with LPS. These data demonstrate that ApoE analogs can inhibit calcineurin signaling, and may be one mechanism by which ApoE analogs modulate the inflammatory response.

Example 9

ApoE Analogs with Enhanced Efficacy in Vitro

We have identified several novel ApoE analogs that exhibit improved characteristics compared to COG 133, such as enhanced potency and efficacy in both in vitro and in vivo models of inflammation and/or neuroprotection, enhanced remyelination-promoting activity, increased stability and increased blood brain barrier (BBB) penetration, as well as decreased toxicity. The following ApoE analogs, COG 112, COG 1410, COG 241, COG 248, COG 68, and COG 345, have been identified as having improved properties as compared to the ApoE peptide, COG 133. COG 125 (a truncated version of COG 1410) did not exhibit any anti-inflammatory properties in vitro or in vivo and is used routinely as a negative control.

TABLE 1

ApoE Analog Sequences

| | | | |
|---|---|---|---|
| COG 133 | SEQ ID NO: 1 | acetyl-LRVRLASHLRKLRKRLL-amide |
| COG 1410 | SEQ ID NO: 2 | acetyl-AS-Aib-LRKL-Aib-KRLL-amide |
| COG 248 | SEQ ID NO: 3 | acetyl-LRVRLAS-Aib-LRKLRK(nitro-Arg)LL-amide |
| COG 345 | SEQ ID NO: 4 | acetyl-LRVRLAS-Aib-LRKLRK(acetyl-Arg)LL-amide |
| COG 112 | SEQ ID NO: 5 | acetyl-RQIKIWFQNRRMKWKKCLRVRLASHLRKLRKRLL-amide |
| COG 241 | SEQ ID NO: 6 | acetyl-Aib-LRKL-Aib-(n acetyl K)RLL-amide |
| COG 68 | SEQ ID NO: 7 | acetyl-RRLSYSRRRFLRVRLASHLRKLRKRLL-amide |
| COG 125 | SEQ ID NO: 8 | acetyl-AS-Aib-LRKL-Aib-KR-amide |

Figure 16:
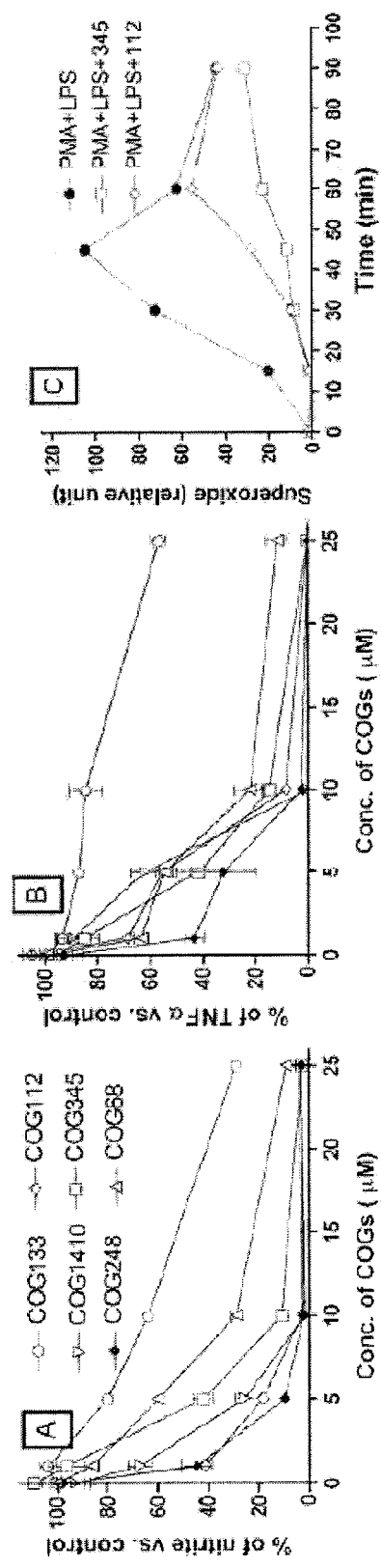
FIG. 16. ApoE analogs suppress the release of nitric oxide (A) and TNF-α (B) in LPS-treated BV2 microglia cells. Series concentrations of ApoE analogs were added to culture medium together with LPS (10 ng/ml). 24 hours later, culture medium was collected for measurement of NO by Griess assay or TNF-α by ELISA. (C) ApoE analogs inhibit superoxide formation in PMA+LPS-treated human macrophage cell line U937. ApoE analogs (10 μM) were added to the cell medium of human macrophage U937 5 minutes prior to PMA+LPS treatment. The release of superoxide in culture medium was measured by Luminol assay kit (Calbiochem).

The murine microglia cell line BV2 was used as the first screening platform to compare the potency of ApoE analogs in anti-inflammatory activity. In response to LPS, BV2 produces amounts of reactive radical NO and inflammatory cytokines, such as TNF-α and IL-6. We stimulated the cells with LPS (10 ng/ml) in the presence of several concentrations of each of the ApoE analogs. We measured NO in medium by Griess assay and TNF-α by ELISA 24 hours after LPS stimulation of the cells. The $IC_{50}$ value was calculated for each of the ApoE analogs. As shown in FIGS. 16A and B, the activity of COG 1410, COG 68, COG 112, COG 345, and COG 248 was clearly superior to that of COG 133 in suppression of microglia activation.

To determine the anti-oxidant effect of the different ApoE analogs, the human macrophage cell line U937 was differentiated with IFN-γ (40 U/ml) for 4 days and treated with phorbol-12-myristate-13-acetate (PMA) and LPS with or without ApoE analogs (10 μM). The release of superoxide in the medium was measured by Luminol Superoxide Assay kit (Calbiochem, CA). Both COG 112 and COG 345 significantly inhibited superoxide release during inflammation (FIG. 16C).

Figure 17:
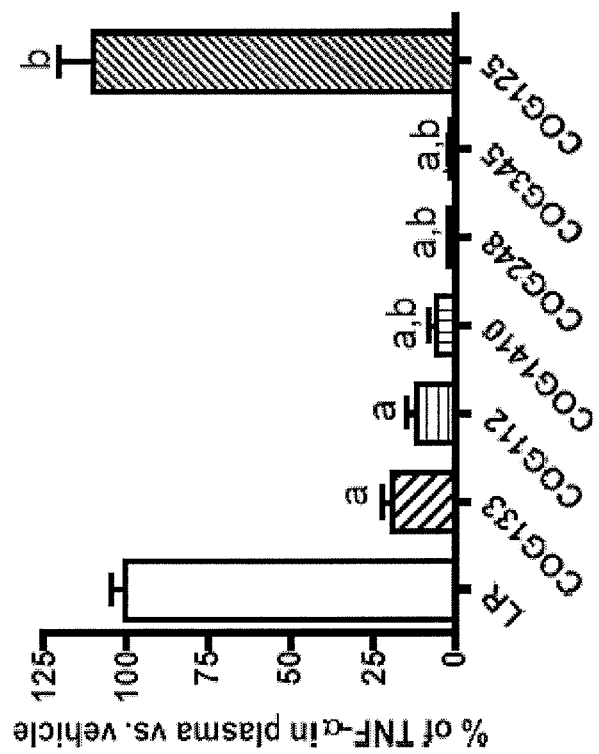
FIG. 17. ApoE analogs suppress LPS-induced TNF-α production in plasma of C57BL mice. Mice received i.p. injection of LPS (1 mg/kg). Five minutes later, they were given COG 133 (4 mg/kg, i.v.) or molar equivalent doses of the indicated ApoE analogs. Whole blood was collected 1 hour after LPS injection, and the level of TNF-α in plasma was quantified by ELISA. The level of plasma TNF-α is expressed as percent of TNF-α production in plasma vs. vehicle control (LR buffer). ANOVA was used for statistical analysis followed by Newman-Keuls Multiple Comparison Test. a=p<0.001 compared to LR group; b=p<0.05 compared to COG 133 group.

The activity of four of the analogs was compared to that of COG 133 using an in vivo model of inflammation. Groups of five mice received i.p. injection of LPS (1 mg/kg). Within 5 min, they were given COG 133 (4 mg/kg, i.v.) or molar equivalent dose of COG 112, COG 1410, COG 248, COG 345, or COG 125 (negative control). Whole blood was collected 1 hour after LPS injection. The level of TNF-α in plasma was quantified with ELISA and expressed as percent of TNF-α production in plasma vs. vehicle control (LR buffer). All of the ApoE analogs demonstrated enhanced suppression of TNF-α release as compared to COG 133 (FIG. 17).

Figure 18:
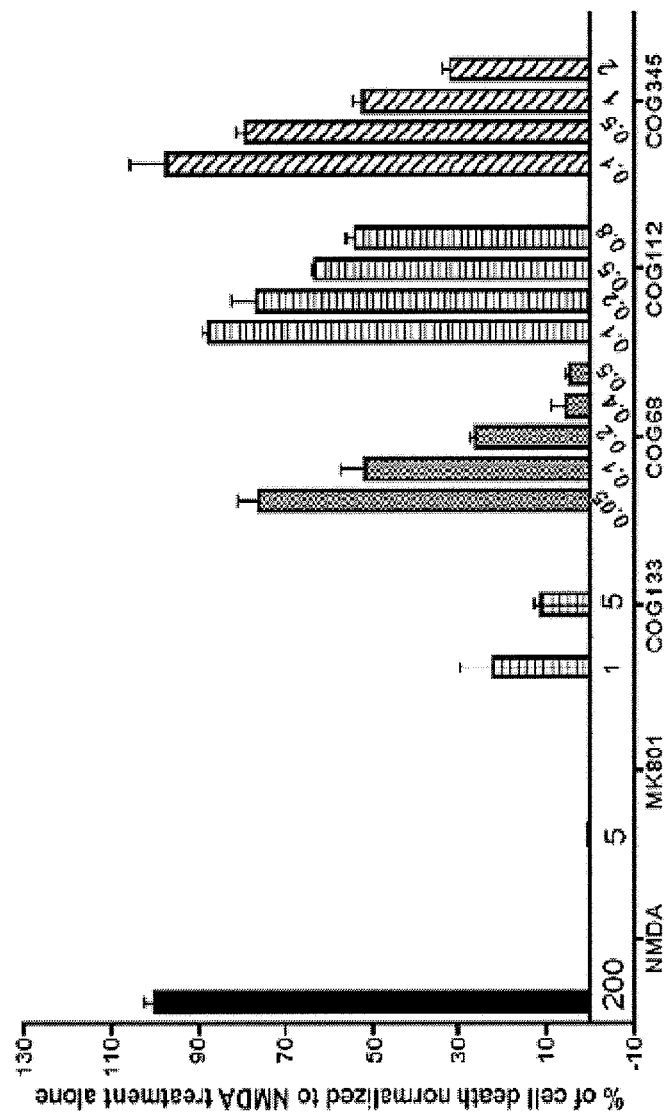
FIG. 18. Comparison of anti-excitotoxicity activity of ApoE analogs in primary neuron-glia mixed culture. Primary neurons growing on an astrocyte layer for 14 days were treated with the indicated concentrations of the ApoE analogs for 15 min. NMDA was then added to the medium to a final concentration of 200 μM. After incubation for 5 min, NMDA-containing medium was replaced with fresh medium with the same ApoE peptides at the designated concentration. After 24 hours, LDH in medium was measured and used as index of cell death. The wells treated with NMDA for 24 hours were considered 100% cell death and used for normalization with the other treatments.

In addition to testing their anti-inflammatory activities, we compared the anti-excitotoxicity activity of the novel ApoE analogs. Primary neurons growing on an astrocyte layer for 14 days were treated with COG 133, COG 68, COG 112, or COG 345 for 15 min NMDA was subsequently added to the medium to a final concentration of 200 μM. After incubation for 5 minutes, the NMDA-containing medium was replaced with fresh medium with the same ApoE analogs at the designated concentration. After 24 hours, LDH in the medium was measured and used as an index of cell death (FIG. 18). The wells treated with NMDA alone for 24 hours were considered 100% cell death and used for normalization with the other treatments. MK801 is a NMDA-receptor antagonist and was used as a negative control.

Example 10

Novel ApoE Analogs Promote Remyelination and Protect Oligodendrocyte Precursor Cells from Cell Death We tested the remyelinating effect of COG 345 on the lysolecithin-induced demyelination model of cerebellum slice culture. As described in Example 4, cerebellar slices obtained from P10 rat pups were first incubated with lysolecithin (0.5 mg/ml) for 16 hours to induce demyelination. Three days after lysolecithin exposure, 1 μM COG 345 (SEQ ID NO: 4) or COG 112 (SEQ ID NO: 5) was added to fresh medium and the slice was incubated for 4 days. Slices were fixed and double stained with myelin marker MBP (green) and Purkinje cell marker calbindin (red). As shown in FIG. 19A-D, COG 345 treatment dramatically restored myelination similar to COG 112, suggesting COG 345 is capable of promoting remyelination.

Figure 19:
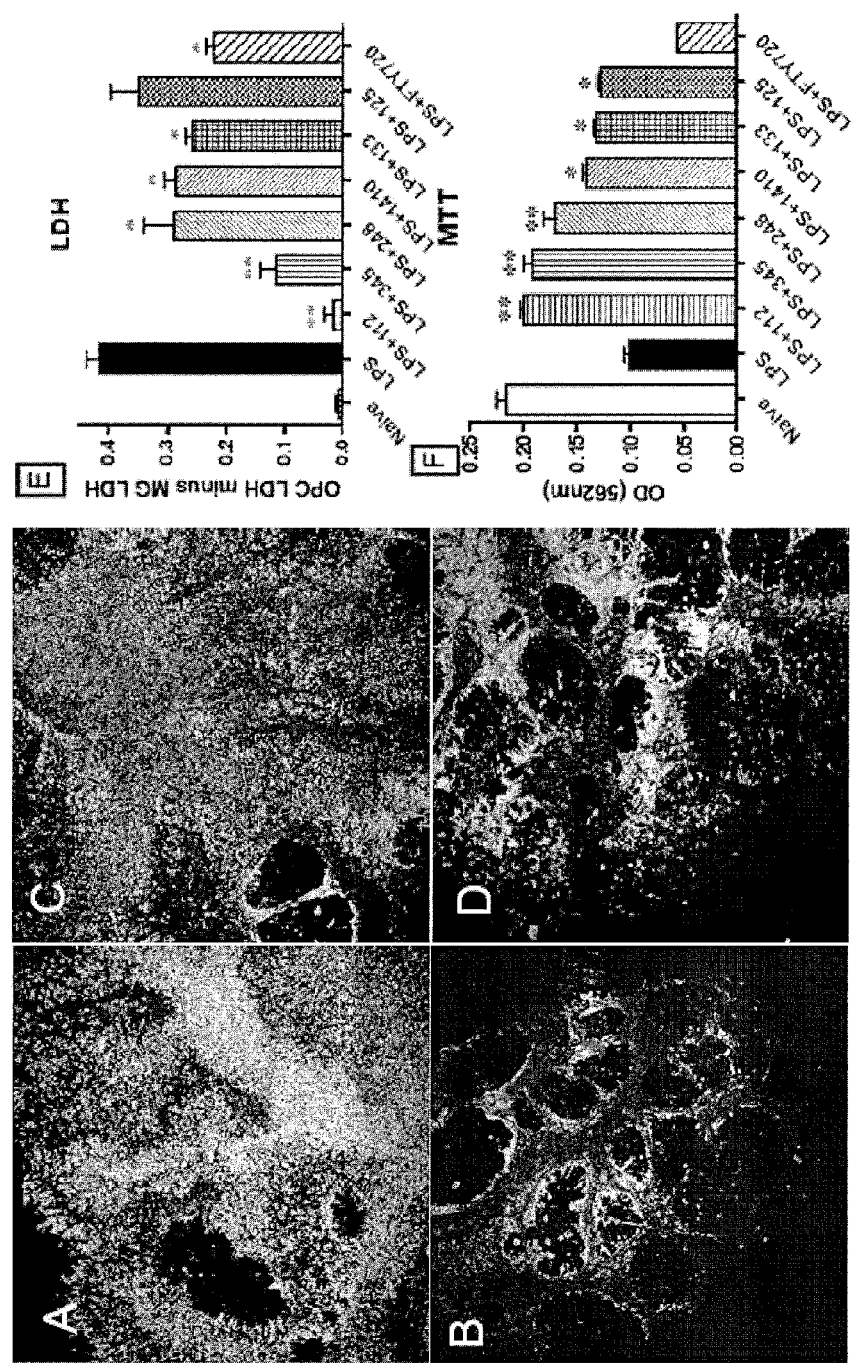
FIG. 19. COG 345 promotes remyelination in lysolecithin-induced demyelination model of cerebellum slices. Significant demyelination was induced by lysolecithin (0.5 mg/ml) in cerebellar slices. COG 112 or COG 345 (1 μM) was added on day 3 when full demyelination was achieved. 4 days later, the slices were fixed and double stained with myelin marker MBP (green) and Purkinje cell marker calbindin (red). (A) Untreated-slices; (B) lysolecithin-treated slices; (C) COG 112-treated slices after lysolecithin exposure; (D) COG 345-treated slices after lysolecithin exposure. E-F. ApoE analogs protect OPCs from LPS-induced cell death in OPC/microglia mixed culture. OPCs and microglia derived from brain culture of P2 rat pups were plated in 96-well plates in 1:1 ratio. LPS (10 ng/ml) together with 1 μM of the indicated ApoE analogs was added to the cultures. After 24 hours, OPC cell death was quantified by LDH assay (E) and MTT assay (F). Statistical analysis was conducted by one-way ANOVA followed by Dunnett comparison vs. LPS group. * P<0.01, ** P<0.001, n=3.

To further assess the ability of the novel ApoE analogs to promote remyelination, the effect of the analogs on OPC survival was assessed in an OPC/microglia mixed culture. OPC and microglia derived from primary culture of P2 rat pup brain were plated on 96-well plates in 1:1 ratio. LPS (10 ng/ml) was added together with 1 μM COG 112, COG 345, COG 248, COG 1410, COG 133, COG 125 (negative control) or FTY720. FTY720 is an immunosuppressive agonist for sphingosine-1-phosphate (S1P) receptors and is currently in clinical trials for treating multiple sclerosis. After 24 hours, cell death of OPC was quantified by both LDH and MTT assays. All ApoE analogs significantly reduced OPC cell death mediated by microglia after stimulation with LPS, with COG 112 and COG 345 being the most potent (FIGS. 19E and F). In contrast, FTY720 did not show a clear protective effect.

To further compare the activity of the various ApoE analogs, the efficacy of the analogs was assessed in a PLP-induced relapsing-remitting experimental autoimmune encephalomyelitis (EAE) model. The first dose of the ApoE analog (4 mg/kg, s.c.) or vehicle (LR) was started on the day when the animals exhibited a clinical score (CS)≥1.5. The second dose was administered the next day followed by three times a week (M, W, F). The results are summarized in Table 2. Relapse rate represents the number of animals experiencing a relapse, while the CSmax indicates the maximal clinical score during relapse. Area under curve represents the area under the curve in a plot of clinical score vs. days post-inoculation (out to 60 days). In particular, COG 248 and COG 345 exhibited a significant improvement in relapse rate and maximum clinical score during relapse. The improvement in relapse rate and clinical score in the EAE model by ApoE analog treatment may be due, in part, to the remyelination-promoting effect of the ApoE analogs.

TABLE 2

Efficacy of ApoE Analogs on PLP EAE Model

| Treatment | Relapse Rate | $CS_{max}$ during relapse (mean ± SEM) | Area under curve (mean ± SEM) |
| --- | --- | --- | --- |
| LR | 7/14 | 3.7 ± 0.7 | 37.4 ± 12.9 |
| COG133 | 7/14 | 3.2 ± 0.7 | 25.3 ± 8.3 |
| COG112 | 5/14 | 2.4 ± 0.8 | 16.7 ± 3.6 |
| COG241 | 8/15 | 2.3 ± 0.8 | 13.5 ± 2.6 |
| COG248 | 4/14 | 1.6 ± 0.2 | 14.0 ± 2.2 |
| COG345 | 4/15 | 1.4 ± 0.2 | 15.5 ± 2.5 |

To fully evaluate the use of ApoE analogs as therapeutic compounds, the margin of safety should also be determined. Towards that end, we determined the maximum tolerated dose of COG 112, COG 248, and COG 345 when administered by intravenous and subcutaneous injection. The results of this analysis is given in Table 3. For all compounds except COG 133, efficacy in an animal model of human diseases has been demonstrated and a safety window of greater than 20 (the maximum tolerated dose/minimum effective dose) by i.v. injection and of >100 for s.c. has been established. In the case of COG 345, this analog demonstrated a superior safety profile by intravenous injection compared to the other analogs when compared on a molar basis.

TABLE 3

Maximum Tolerated Dose and Minimum Effective Dose of ApoE Analogs

| Compound | Maximum Tolerated Dose | | Minimum Effective Dose (model) |
| --- | --- | --- | --- |
| | Intravenous | Subcutaneous | |
| COG133 | 16 mg/kg | >100 mg/kg | 1 mg/kg (CIA, EAE) |
| COG112 | 28 mg/kg | >100 mg/kg | 1 mg/kg (EAE, TBI) |
| COG248 | 25 mg/kg | >150 mg/kg | 1 mg/kg (EAE) |
| COG345 | 20~25 mg/kg | >150 mg/kg | 1 mg/kg (EAE) |

EAE—Experimental Autoimmune Encephalomyelitis,
TBI - Controlled Cortical Impact TBI It is understood that the disclosed invention is not limited to the particular methodology, protocols and reagents described as these may vary. It is also understood that the terminology used herein is for the purposes of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the exemplary methods, devices, and materials are as described. All patents, patent applications and other publications cited herein and the materials for which they are cited are specifically incorporated by reference in their entireties.

Those skilled in the art will recognize, or be able to ascertain using no more than routine experimentation, many equivalents to the specific embodiments of the invention described herein. Such equivalents are intended to be encompassed by the following claims.

TABLE 1

Other Suitable ApoE Analogs

| | |
|---|---|
| LRVRLASH-(NMe)-L-RKLRKRLL-NH₂ | Ac-AS-Aib-LRKL-Aib-K(dmarg)LL-NH₂ |
| Ac-ASH-Aib-RKLRKRLL-NH₂ | Ac-AS-Aib-LRKL-Aib-ARLL-NH₂ |
| Ac-AS-Aib-LRKLRKRLL-NH₂ | Ac-AS-Aib-LRKL-Aib-(sclys)RLL-NH₂ |
| Ac-DS-Aib-LRKLRKRLL-NH₂ | Ac-AS-Aib-LRKL-Aib-(azlys)RLL-NH₂ |
| Ac-ASHLRKL-Aib-KRLL-NH₂ | Ac-ASH-Aib-RKL-Aib-KRLL-NH₂ |
| Ac-AS-Aib-LRKL-Aib-KRLL-NH₂ | Ac-AS-Aib-LRKL-Aib-KRL-(NLe)-NH₂ |
| Ac-DR-Aib-ASHLRKLRKR-Aib-L-NH₂ | Ac-AS-Aib-LRKL-Aib-KR-(NLe)-L-NH₂ |
| Ac-DS-Aib-LRKLRKR-Aib-L-NH₂ | Ac-AS-Aib-LRKL-Aib-KR-(NLe)-(Nle)-NH₂ |
| Ac-DR-Aib-ASHLRKL-Aib-KRLL-NH₂ | Ac-AS-Aib-LRKL-Aib-K(om)L-(NLe)-NH₂ |
| Ac-DS-Aib-LRKL-Aib-KRLL-NH₂ | Ac-AS-Aib-LRKL-Aib-K(om)-(NLe)-L-NH₂ |
| Ac-DR-Aib-AS-Aib-LRKLRKRLL-NH₂ | Ac-AS-Aib-LRKL-Aib-K(om)-(NLe)-(Nle)-NH₂ |
| Ac-DR-Aib-ASHLRKLRKRLL-NH₂ | Ac-AS-Aib-LRKL-Aib-K(harg)L-(NLe)-NH₂ |
| Ac-CAS-Aib-LRKL-Aib-KRLL-NH₂ | Ac-AS-Aib-LRKL-Aib-K(harg)-(NLe)-L-NH₂ |
| Ac-DS-Aib-LRKL-Aib-KRLL-NH₂ | Ac-AS-Aib-LRKL-Aib-K(harg)-(NLe)-(Nle)-NH₂ |
| Ac-AS-Aib-LRKL-Aib-KRLV-NH₂ | Ac-AS-Aib-L(om)KL-Aib-KRLL-NH₂ |
| Ac-AS-Aib-LRKL-Aib-KRLM-NH₂ | Ac-AS-Aib-L(om)KL-Aib-K(om)LL-NH₂ |
| Ac-AS-Aib-LRKL-Aib-KRLI-NH₂ | Ac-AS-Aib-L(om)KL-Aib-KRL-(NLe)-NH₂ |
| Ac-AS-Aib-LRKL-Aib-KRLA-NH₂ | Ac-AS-Aib-L(om)KL-Aib-KRL-(NLe)-(NLe)-NH₂ |
| Ac-AS-Aib-LRKL-Aib-KALL-NH₂ | Ac-AS-Aib-L(om)KL-Aib-K(om)L-(Nle)-NH₂ |
| Ac-AS-Aib-LRKL-Aib-K(om)LL-NH₂ | Ac-AS-Aib-L(om)KL-Aib-K(om)-(NLe)-(Nle)-NH₂ |
| Ac-AS-Aib-LRKL-Aib-K(narg)LL-NH₂ | Ac-ASHLRKLRKRLL-NH₂ (apoe138-149) |
| Ac-AS-Aib-LRKL-Aib-K(harg)LL-NH₂ | Ac-ASHCRKLCKRLL-NH₂ |
| | Ac-ASCLRKLCKRLL-NH₂ |
| | Ac-CSHLRKLCKRLL-NH₂ |
| | Ac-ASHLRKCRKRCL-NH₂ |
| | Ac-ASHCRKLRKRCL-NH₂ |

---

The invention claimed is:

1. A method of promoting remyelination in a subject in need thereof comprising administering to the subject a composition comprising a pharmaceutically acceptable carrier and an effective amount of at least one ApoE peptide derivative, wherein said ApoE peptide derivative comprises a consecutive amino acid sequence having at least 75% sequence identity to the sequence of SEQ ID NO: 1, and wherein myelination is enhanced in the subject following administration of the composition.

2. The method of claim 1, wherein the subject is suffering from a demyelinating disorder or condition.

3. The method of claim 2, wherein the demyelinating disorder or condition is selected from the group consisting of optic neuritis, devic disease, transverse myelitis, acute disseminated encephalomyelitis, adrenoleukodystrophy, adrenomyeloneuropathy, Guillain-Barre syndrome, Chronic Inflammatory Demyelinating Polyneuropathy (CIDP), and diabetic peripheral neuropathy.

4. The method of claim 1, wherein the subject has a spinal cord or nerve injury.

5. The method of claim 1, wherein the peptide derivative comprises a consecutive amino acid sequence having at least 85% sequence identity to the sequence of SEQ ID NO: 1.

6. The method of claim 1, wherein the peptide derivative contains a sequence selected from the group consisting of:

```
                                          (SEQ ID NO: 2)
Ac-As-Aib-LRKL-Aib-KRLL-NH2

(SEQ ID NO: 3)
Ac-LRVRLAS-Aib-LRKLRK(nitro-Arg)LL-NH2, (SEQ ID NO: 4)
Ac-LRVRLAS-Aib-LRKLRK(acetyl-Arg)LL-NH2,
and (SEQ ID NO: 6)
Ac-Aib-LRKL-Aib-(n acetyl K)RLL-NH2,
``` wherein Aib is amino iso-butyric acid, (nitro-Arg) is nitro arginine, (acetyl-Arg) is acetyl arginine, (n acetyl K) is n-acetyl lysine, and Ac is an acetylated amino terminus.

7. The method of claim 1, wherein the peptide derivative is conjugated to a protein transduction domain (PTD) from antennapedia, TAT, SynB1, SynB3, SynB5, or polyarginine.

8. The method of claim 7, wherein the peptide conjugate has a sequence of Ac-RQIKIWFQNRRMKWKKCLRVR-LASHLRKLRKRLL-NH2 (SEQ ID NO: 5) or Ac-RRLSYS-RRRFLRVRLASHLRKLRKRLL-NH2 (SEQ ID NO: 7).

9. The method of claim 1, wherein the number of oligodendrocytes is increased in the subject following administration of the composition.

10. The method of claim 1, wherein neuronal inflammation is decreased in the subject following administration of the composition.

11. The method of claim 1, wherein one or more symptoms of demyelination is reduced in the subject following administration of the composition.

12. The method of claim 4, wherein the spinal cord injury is a contusive injury or a compressive injury.

13. The method of claim 4, wherein the nerve injury is a peripheral nerve crush injury.

14. The method of claim 7, wherein the protein transduction domain comprises a sequence of SEQ ID NO: 10 or SEQ ID NO: 11.

15. The method of claim 1, wherein the peptide derivative is no more than 50 amino acids in length.

16. The method of claim 7, wherein the protein transduction domain comprises a sequence of SEQ ID NO: 12, SEQ ID NO: 13, or SEQ ID NO: 14.

17. A method of promoting remyelination in a subject in need thereof comprising administering to the subject an effective amount of a vector containing a nucleic acid sequence encoding an ApoE peptide derivative, wherein said ApoE peptide derivative comprises a consecutive amino acid sequence having at least 75% sequence identity to the sequence of SEQ ID NO: 1, and wherein myelination is enhanced in the subject following administration of the vector.

18. The method of claim 17, wherein the vector is a viral vector.

19. The method of claim 18, wherein the viral vector is a herpesviral vector, an adenoviral vector, or a lentiviral vector.

20. The method of claim 17, wherein the subject is suffering from a demyelinating disorder or condition.

21. The method of claim 20, wherein the demyelinating disorder or condition is selected from the group consisting of optic neuritis, devic disease, transverse myelitis, acute disseminated encephalomyelitis, adrenoleukodystrophy, adrenomyeloneuropathy, Guillain-Barre syndrome, Chronic Inflammatory Demyelinating Polyneuropathy (CIDP), and diabetic peripheral neuropathy.

22. The method of claim 17, wherein the subject has a spinal cord or nerve injury.

23. The method of claim 22, wherein the spinal cord injury is a contusive injury or a compressive injury.

24. The method of claim 22, wherein the nerve injury is a peripheral nerve crush injury.

25. The method of claim 17, wherein the peptide derivative comprises a consecutive amino acid sequence having at least 85% sequence identity to the sequence of SEQ ID NO: 1.

26. The method of claim 17, wherein the peptide derivative comprises the sequence of SEQ ID NO: 1.

27. The method of claim 17, wherein the nucleic acid encodes the peptide derivative conjugated to a protein transduction domain (PTD) from antennapedia, TAT, SynB1, SynB3, SynB5, or polyarginine.

28. The method of claim 27, wherein the protein transduction domain comprises a sequence of SEQ ID NO: 10 or SEQ ID NO: 11.

29. The method of claim 27, wherein the protein transduction domain comprises a sequence of SEQ ID NO: 12, SEQ ID NO: 13, or SEQ ID NO: 14.

30. The method of claim 17, wherein the number of oligodendrocytes is increased in the subject following administration of the composition.

31. The method of claim 17, wherein neuronal inflammation is decreased in the subject following administration of the composition.

32. The method of claim 17, wherein one or more symptoms of demyelination is reduced in the subject following administration of the composition.

33. The method of claim 17, wherein the peptide derivative is no more than 50 amino acids in length.

34. The method of claim 1, wherein the peptide derivative comprises the sequence of SEQ ID NO: 1.

35. The method of claim 27, wherein the nucleic acid encodes a peptide conjugate which comprises SEQ ID NO:5 or SEQ ID NO:7.

* * * * *

UNITED STATES PATENT AND TRADEMARK OFFICE
CERTIFICATE OF CORRECTION

PATENT NO. : 8,629,242 B2  Page 1 of 1
APPLICATION NO. : 12/671433
DATED : January 14, 2014
INVENTOR(S) : Vitek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 805 days.

Signed and Sealed this
Thirtieth Day of May, 2017

Michelle K. Lee
*Director of the United States Patent and Trademark Office*

SEQUENCE LISTING

<160> NUMBER OF SEQ ID NOS: 64

<210> SEQ ID NO 1
<211> LENGTH: 17
<212> TYPE: PRT
<213> ORGANISM: Artificial Sequence
<220> FEATURE:
<223> OTHER INFORMATION: ApoE mimetic peptide

<400> SEQUENCE: 1

Leu Arg Val Arg Leu Ala Ser His Leu Arg Lys Leu Arg Lys Arg Leu
1               5                   10                  15

Leu

<210> SEQ ID NO 2

```
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 2

Ala Ser Xaa Leu Arg Lys Leu Xaa Lys Arg Leu Leu
1               5                   10

<210> SEQ ID NO 3
<211> LENGTH: 17
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Leu may be acetylated
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (15)..(15)
<223> OTHER INFORMATION: Xaa may be nitroarginine
<220> FEATURE:
<221> NAME/KEY: misc_feature
<222> LOCATION: (17)..(17)
<223> OTHER INFORMATION: Leu may be amidated

<400> SEQUENCE: 3

Leu Arg Val Arg Leu Ala Ser Xaa Leu Arg Lys Leu Arg Lys Xaa Leu
1               5                   10                  15

Leu

<210> SEQ ID NO 4
<211> LENGTH: 17
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Leu may be acetylated
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (15)..(15)
<223> OTHER INFORMATION: Arg may be acetylated
<220> FEATURE:
<221> NAME/KEY: misc_feature
<222> LOCATION: (17)..(17)
```

<223> OTHER INFORMATION: Leu may be amidated

<400> SEQUENCE: 4

Leu Arg Val Arg Leu Ala Ser Xaa Leu Arg Lys Leu Arg Lys Arg Leu
1               5                   10                  15

Leu

<210> SEQ ID NO 5
<211> LENGTH: 34
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Arg may be acetylated
<220> FEATURE:
<221> NAME/KEY: misc_feature
<222> LOCATION: (34)..(34)
<223> OTHER INFORMATION: Leu may be amidated

<400> SEQUENCE: 5

Arg Gln Ile Lys Ile Trp Phe Gln Asn Arg Arg Met Lys Trp Lys Lys
1               5                   10                  15

Cys Leu Arg Val Arg Leu Ala Ser His Leu Arg Lys Leu Arg Lys Arg
            20                  25                  30

Leu Leu

<210> SEQ ID NO 6
<211> LENGTH: 10
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Xaa may be alpha-aminoisobutyric acid
<220> FEATURE:
<221> NAME/KEY: misc_feature
<222> LOCATION: (1)..(1)
<223> OTHER INFORMATION: Alpha-aminoisobutyric acid may be acetylated
<220> FEATURE:
<221> NAME/KEY: misc_feature
<222> LOCATION: (6)..(6)
<223> OTHER INFORMATION: Xaa may be alpha-aminoisobutyric acid
<220> FEATURE:
<221> NAME/KEY: misc_feature
<222> LOCATION: (7)..(7)
<223> OTHER INFORMATION: Lys may be N-acetylated
<220> FEATURE:
<221> NAME/KEY: misc_feature
<222> LOCATION: (10)..(10)
<223> OTHER INFORMATION: Leu may be amidated

<400> SEQUENCE: 6

Xaa Leu Arg Lys Leu Xaa Lys Arg Leu Leu
1               5                   10

<210> SEQ ID NO 7
<211> LENGTH: 27
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Arg may be acetylated
<220> FEATURE:

```
<221> NAME/KEY: misc_feature
<222> LOCATION: (27)..(27)
<223> OTHER INFORMATION: Leu may be amidated

<400> SEQUENCE: 7

Arg Arg Leu Ser Tyr Ser Arg Arg Phe Leu Arg Val Arg Leu Ala
1               5                   10                  15

Ser His Leu Arg Lys Leu Arg Lys Arg Leu Leu
            20                  25

<210> SEQ ID NO 8
<211> LENGTH: 10
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Arg may be amidated

<400> SEQUENCE: 8

Ala Ser Xaa Leu Arg Lys Leu Xaa Lys Arg
1               5                   10

<210> SEQ ID NO 9
<211> LENGTH: 13
<212> TYPE: PRT
<213> ORGANISM: Unknown
<220> FEATURE:
<223> OTHER INFORMATION: Protein transduction domain peptide

<400> SEQUENCE: 9

Gly Arg Lys Lys Arg Arg Gln Arg Arg Arg Pro Pro Gln
1               5                   10

<210> SEQ ID NO 10
<211> LENGTH: 16
<212> TYPE: PRT
<213> ORGANISM: Unknown
<220> FEATURE:
<223> OTHER INFORMATION: Protein transduction domain peptide

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 7
<212> TYPE: PRT
<213> ORGANISM: Unknown
<220> FEATURE:
<223> OTHER INFORMATION: Protein transduction domain peptide

<400> SEQUENCE: 11

Arg Arg Met Lys Trp Lys Lys
1               5
```

```
<210> SEQ ID NO 12
<211> LENGTH: 18
<212> TYPE: PRT
<213> ORGANISM: Unknown
<220> FEATURE:
<223> OTHER INFORMATION: Protein transduction domain peptide

<400> SEQUENCE: 12

Arg Gly Gly Arg Leu Ser Tyr Ser Arg Arg Phe Ser Thr Ser Thr
1               5                   10                  15

Gly Arg

<210> SEQ ID NO 13
<211> LENGTH: 10
<212> TYPE: PRT
<213> ORGANISM: Unknown
<220> FEATURE:
<223> OTHER INFORMATION: Protein transduction domain peptide

<400> SEQUENCE: 13

Arg Arg Leu Ser Tyr Ser Arg Arg Arg Phe
1               5                   10

<210> SEQ ID NO 14
<211> LENGTH: 17
<212> TYPE: PRT
<213> ORGANISM: Unknown
<220> FEATURE:
<223> OTHER INFORMATION: Protein transduction domain peptide

<400> SEQUENCE: 14

Arg Gly Gly Arg Leu Ala Tyr Leu Arg Arg Arg Trp Ala Val Leu Gly
1               5                   10                  15

Arg

<210> SEQ ID NO 15
<211> LENGTH: 8
<212> TYPE: PRT
<213> ORGANISM: Unknown
<220> FEATURE:
<223> OTHER INFORMATION: Protein transduction domain peptide

<400> SEQUENCE: 15

Arg Arg Arg Arg Arg Arg Arg Arg
1               5

<210> SEQ ID NO 16
<211> LENGTH: 17
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (9)..(9)
<223> OTHER INFORMATION: Leu may be N-methylated
<220> FEATURE:
<221> NAME/KEY: misc_feature
<222> LOCATION: (17)..(17)
<223> OTHER INFORMATION: Leu may be amidated

<400> SEQUENCE: 16

Leu Arg Val Arg Leu Ala Ser His Leu Arg Lys Leu Arg Lys Arg Leu
1               5                   10                  15

Leu
```

```
<210> SEQ ID NO 17
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (4)..(4)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 17

Ala Ser His Xaa Arg Lys Leu Arg Lys Arg Leu Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 18

Ala Ser Xaa Leu Arg Lys Leu Arg Lys Arg Leu Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 19

Asp Ser Xaa Leu Arg Lys Leu Arg Lys Arg Leu Leu
1               5                   10

<210> SEQ ID NO 20
<211> LENGTH: 12
<212> TYPE: PRT
<213> ORGANISM: Artificial Sequence
<220> FEATURE:
```

```
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 20

Ala Ser His Leu Arg Lys Leu Xaa Lys Arg Leu Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 21

Ala Ser Xaa Leu Arg Lys Leu Xaa Lys Arg Leu Leu
1               5                   10

<210> SEQ ID NO 22
<211> LENGTH: 15
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (14)..(14)
<223> OTHER INFORMATION: Xaa may be alpha-aminoisobutyric acid
<220> FEATURE:
<221> NAME/KEY: misc_feature
<222> LOCATION: (15)..(15)
<223> OTHER INFORMATION: Leu may be amidated

<400> SEQUENCE: 22

Asp Arg Xaa Ala Ser His Leu Arg Lys Leu Arg Lys Arg Xaa Leu
1               5                   10                  15

<210> SEQ ID NO 23
<211> LENGTH: 12
```

```
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (11)..(11)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 23

Asp Ser Xaa Leu Arg Lys Leu Arg Lys Arg Xaa Leu
1               5                   10

<210> SEQ ID NO 24
<211> LENGTH: 15
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (11)..(11)
<223> OTHER INFORMATION: Xaa may be alpha-aminoisobutyric acid
<220> FEATURE:
<221> NAME/KEY: misc_feature
<222> LOCATION: (15)..(15)
<223> OTHER INFORMATION: Leu may be amidated

<400> SEQUENCE: 24

Asp Arg Xaa Ala Ser His Leu Arg Lys Leu Xaa Lys Arg Leu Leu
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 25
```

```
Asp Ser Xaa Leu Arg Lys Leu Xaa Lys Arg Leu Leu
1               5                   10
```

<210> SEQ ID NO 26
<211> LENGTH: 15
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (6)..(6)
<223> OTHER INFORMATION: Xaa may be alpha-aminoisobutyric acid
<220> FEATURE:
<221> NAME/KEY: misc_feature
<222> LOCATION: (15)..(15)
<223> OTHER INFORMATION: Leu may be amidated

<400> SEQUENCE: 26

```
Asp Arg Xaa Ala Ser Xaa Leu Arg Lys Leu Arg Lys Arg Leu Leu
1               5                   10                  15
```

<210> SEQ ID NO 27
<211> LENGTH: 15
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (15)..(15)
<223> OTHER INFORMATION: Leu may be amidated

<400> SEQUENCE: 27

```
Asp Arg Xaa Ala Ser His Leu Arg Lys Leu Arg Lys Arg Leu Leu
1               5                   10                  15
```

<210> SEQ ID NO 28
<211> LENGTH: 13
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Cys may be acetylated
<220> FEATURE:
<221> NAME/KEY: misc_feature
<222> LOCATION: (4)..(4)
<223> OTHER INFORMATION: Xaa may be alpha-aminoisobutyric acid
<220> FEATURE:
<221> NAME/KEY: misc_feature
<222> LOCATION: (9)..(9)
<223> OTHER INFORMATION: Xaa may be alpha-aminoisobutyric acid
<220> FEATURE:
<221> NAME/KEY: misc_feature
<222> LOCATION: (13)..(13)

<223> OTHER INFORMATION: Leu may be amidated

<400> SEQUENCE: 28

Cys Ala Ser Xaa Leu Arg Lys Leu Xaa Lys Arg Leu Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Asp may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 29

Asp Ser Xaa Leu Arg Lys Leu Xaa Lys Arg Leu Leu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Val may be amidated

<400> SEQUENCE: 30

Ala Ser Xaa Leu Arg Lys Leu Xaa Lys Arg Leu Val
1               5                   10

<210> SEQ ID NO 31
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid

```
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Met may be amidated

<400> SEQUENCE: 31

Ala Ser Xaa Leu Arg Lys Leu Xaa Lys Arg Leu Met
1               5                   10

<210> SEQ ID NO 32
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Ile may be amidated

<400> SEQUENCE: 32

Ala Ser Xaa Leu Arg Lys Leu Xaa Lys Arg Leu Ile
1               5                   10

<210> SEQ ID NO 33
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Ala may be amidated

<400> SEQUENCE: 33

Ala Ser Xaa Leu Arg Lys Leu Xaa Lys Arg Leu Ala
1               5                   10

<210> SEQ ID NO 34
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
```

```
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 34

Ala Ser Xaa Leu Arg Lys Leu Xaa Lys Ala Leu Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be ornithine
<220> FEATURE:
<221> NAME/KEY: misc_feature
<222> LOCATION: (12)..(12)
<223> OTHER INFORMATION: Leu may be amidated

<400> SEQUENCE: 35

Ala Ser Xaa Leu Arg Lys Leu Xaa Lys Xaa Leu Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be nitroarginine
<220> FEATURE:
<221> NAME/KEY: misc_feature
<222> LOCATION: (12)..(12)
```

<223> OTHER INFORMATION: Leu may be amidated

<400> SEQUENCE: 36

Ala Ser Xaa Leu Arg Lys Leu Xaa Lys Xaa Leu Leu
1               5                   10

<210> SEQ ID NO 37
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be homoarginine
<220> FEATURE:
<221> NAME/KEY: misc_feature
<222> LOCATION: (12)..(12)
<223> OTHER INFORMATION: Leu may be amidated

<400> SEQUENCE: 37

Ala Ser Xaa Leu Arg Lys Leu Xaa Lys Xaa Leu Leu
1               5                   10

<210> SEQ ID NO 38
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be D-alpha-methylarginine
<220> FEATURE:
<221> NAME/KEY: misc_feature
<222> LOCATION: (12)..(12)
<223> OTHER INFORMATION: Leu may be amidated

<400> SEQUENCE: 38

Ala Ser Xaa Leu Arg Lys Leu Xaa Lys Xaa Leu Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: ApoE mimetic peptide

```
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 39

Ala Ser Xaa Leu Arg Lys Leu Xaa Ala Arg Leu Leu
1               5                   10

<210> SEQ ID NO 40
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (9)..(9)
<223> OTHER INFORMATION: Xaa may be N-alpha-acetyllysine
<220> FEATURE:
<221> NAME/KEY: misc_feature
<222> LOCATION: (12)..(12)
<223> OTHER INFORMATION: Leu may be amidated

<400> SEQUENCE: 40

Ala Ser Xaa Leu Arg Lys Leu Xaa Xaa Arg Leu Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (9)..(9)
<223> OTHER INFORMATION: Xaa may be azalysine
<220> FEATURE:
<221> NAME/KEY: misc_feature
```

```
<222> LOCATION: (12)..(12)
<223> OTHER INFORMATION: Leu may be amidated

<400> SEQUENCE: 41

Ala Ser Xaa Leu Arg Lys Leu Xaa Xaa Arg Leu Leu
1               5                   10

<210> SEQ ID NO 42
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (4)..(4)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 42

Ala Ser His Xaa Arg Lys Leu Xaa Lys Arg Leu Leu
1               5                   10

<210> SEQ ID NO 43
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 43

Ala Ser Xaa Leu Arg Lys Leu Xaa Lys Arg Leu Xaa
1               5                   10

<210> SEQ ID NO 44
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
```

```
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (11)..(11)
<223> OTHER INFORMATION: Xaa may be norleucine
<220> FEATURE:
<221> NAME/KEY: misc_feature
<222> LOCATION: (12)..(12)
<223> OTHER INFORMATION: Leu may be amidated

<400> SEQUENCE: 44

Ala Ser Xaa Leu Arg Lys Leu Xaa Lys Arg Xaa Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (11)..(11)
<223> OTHER INFORMATION: Xaa may be norleucine
<220> FEATURE:
<221> NAME/KEY: misc_feature
<222> LOCATION: (12)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 45

Ala Ser Xaa Leu Arg Lys Leu Xaa Lys Arg Xaa Xaa
1               5                   10

<210> SEQ ID NO 46
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
```

```
<221> NAME/KEY: misc_feature
<222> LOCATION: (10)..(10)
<223> OTHER INFORMATION: Xaa may be ornithine
<220> FEATURE:
<221> NAME/KEY: misc_feature
<222> LOCATION: (12)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 46

Ala Ser Xaa Leu Arg Lys Leu Xaa Lys Xaa Leu Xaa
1               5                   10

<210> SEQ ID NO 47
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be ornithine
<220> FEATURE:
<221> NAME/KEY: misc_feature
<222> LOCATION: (11)..(11)
<223> OTHER INFORMATION: Xaa may be norleucine
<220> FEATURE:
<221> NAME/KEY: misc_feature
<222> LOCATION: (12)..(12)
<223> OTHER INFORMATION: Leu may be amidated

<400> SEQUENCE: 47

Ala Ser Xaa Leu Arg Lys Leu Xaa Lys Xaa Xaa Leu
1               5                   10

<210> SEQ ID NO 48
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be ornithine
<220> FEATURE:
<221> NAME/KEY: misc_feature
<222> LOCATION: (11)..(12)
```

-continued

<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 48

Ala Ser Xaa Leu Arg Lys Leu Xaa Lys Xaa Xaa Xaa
1               5                   10

<210> SEQ ID NO 49
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be homoarginine
<220> FEATURE:
<221> NAME/KEY: misc_feature
<222> LOCATION: (12)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 49

Ala Ser Xaa Leu Arg Lys Leu Xaa Lys Xaa Leu Xaa
1               5                   10

<210> SEQ ID NO 50
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be homoarginine
<220> FEATURE:
<221> NAME/KEY: misc_feature
<222> LOCATION: (11)..(11)
<223> OTHER INFORMATION: Xaa may be norleucine
<220> FEATURE:
<221> NAME/KEY: misc_feature
<222> LOCATION: (12)..(12)
<223> OTHER INFORMATION: Leu may be amidated -continued

```
<400> SEQUENCE: 50

Ala Ser Xaa Leu Arg Lys Leu Xaa Lys Xaa Xaa Leu
1               5                   10

<210> SEQ ID NO 51
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be homoarginine
<220> FEATURE:
<221> NAME/KEY: misc_feature
<222> LOCATION: (11)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 51

Ala Ser Xaa Leu Arg Lys Leu Xaa Lys Xaa Xaa Xaa
1               5                   10

<210> SEQ ID NO 52
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (5)..(5)
<223> OTHER INFORMATION: Xaa may be ornithine
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Leu may be amidated

<400> SEQUENCE: 52

Ala Ser Xaa Leu Xaa Lys Leu Xaa Lys Arg Leu Leu
1               5                   10

<210> SEQ ID NO 53
<211> LENGTH: 12
<212> TYPE: PRT
<213> ORGANISM: Artificial Sequence
```

```
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (5)..(5)
<223> OTHER INFORMATION: Xaa may be ornithine
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be ornithine
<220> FEATURE:
<221> NAME/KEY: misc_feature
<222> LOCATION: (12)..(12)
<223> OTHER INFORMATION: Leu may be amidated

<400> SEQUENCE: 53

Ala Ser Xaa Leu Xaa Lys Leu Xaa Lys Xaa Leu Leu
1               5                   10

<210> SEQ ID NO 54
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (5)..(5)
<223> OTHER INFORMATION: Xaa may be ornithine
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 54

Ala Ser Xaa Leu Xaa Lys Leu Xaa Lys Arg Leu Xaa
1               5                   10

<210> SEQ ID NO 55
<211> LENGTH: 13
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
```

```
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (5)..(5)
<223> OTHER INFORMATION: Xaa may be ornithine
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (12)..(13)
<223> OTHER INFORMATION: Xaa may be norleucine
<220> FEATURE:
<221> NAME/KEY: misc_feature
<222> LOCATION: (13)..(13)
<223> OTHER INFORMATION: Norleucine may be amidated

<400> SEQUENCE: 55

Ala Ser Xaa Leu Xaa Lys Leu Xaa Lys Arg Leu Xaa Xaa
1               5                   10

<210> SEQ ID NO 56
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (5)..(5)
<223> OTHER INFORMATION: Xaa may be ornithine
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be ornithine
<220> FEATURE:
<221> NAME/KEY: misc_feature
<222> LOCATION: (12)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 56

Ala Ser Xaa Leu Xaa Lys Leu Xaa Lys Xaa Leu Xaa
1               5                   10

<210> SEQ ID NO 57
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
```

```
<222> LOCATION: (3)..(3)
<223> OTHER INFORMATION: Xaa may be alpha-aminoisobutyric acid
<220> FEATURE:
<221> NAME/KEY: misc_feature
<222> LOCATION: (5)..(5)
<223> OTHER INFORMATION: Xaa may be ornithine
<220> FEATURE:
<221> NAME/KEY: misc_feature
<222> LOCATION: (8)..(8)
<223> OTHER INFORMATION: Xaa may be alpha-aminoisobutyric acid
<220> FEATURE:
<221> NAME/KEY: misc_feature
<222> LOCATION: (10)..(10)
<223> OTHER INFORMATION: Xaa may be ornithine
<220> FEATURE:
<221> NAME/KEY: misc_feature
<222> LOCATION: (11)..(12)
<223> OTHER INFORMATION: Xaa may be norleucine
<220> FEATURE:
<221> NAME/KEY: misc_feature
<222> LOCATION: (12)..(12)
<223> OTHER INFORMATION: Norleucine may be amidated

<400> SEQUENCE: 57

Ala Ser Xaa Leu Xaa Lys Leu Xaa Lys Xaa Xaa Xaa
1               5                   10

<210> SEQ ID NO 58
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (12)..(12)
<223> OTHER INFORMATION: Leu may be amidated

<400> SEQUENCE: 58

Ala Ser His Leu Arg Lys Leu Arg Lys Arg Leu Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (12)..(12)
<223> OTHER INFORMATION: Leu may be amidated

<400> SEQUENCE: 59

Ala Ser His Cys Arg Lys Leu Cys Lys Arg Leu Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
```

```
<223> OTHER INFORMATION: Ala may be acetylated
<220> FEATURE:
<221> NAME/KEY: misc_feature
<222> LOCATION: (12)..(12)
<223> OTHER INFORMATION: Leu may be amidated

<400> SEQUENCE: 60

Ala Ser Cys Leu Arg Lys Leu Cys Lys Arg Leu Leu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Cys may be acetylated
<220> FEATURE:
<221> NAME/KEY: misc_feature
<222> LOCATION: (12)..(12)
<223> OTHER INFORMATION: Leu may be amidated

<400> SEQUENCE: 61

Cys Ser His Leu Arg Lys Leu Cys Lys Arg Leu Leu
1               5                   10

<210> SEQ ID NO 62
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (12)..(12)
<223> OTHER INFORMATION: Leu may be amidated

<400> SEQUENCE: 62

Ala Ser His Leu Arg Lys Cys Arg Lys Arg Cys Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: ApoE mimetic peptide
<220> FEATURE:
<221> NAME/KEY: misc_feature
<222> LOCATION: (1)..(1)
<223> OTHER INFORMATION: Ala may be acetylated
<220> FEATURE:
<221> NAME/KEY: misc_feature
<222> LOCATION: (12)..(12)
<223> OTHER INFORMATION: Leu may be amidated

<400> SEQUENCE: 63

Ala Ser His Cys Arg Lys Leu Arg Lys Arg Cys Leu
1               5                   10

<210> SEQ ID NO 64
<211> LENGTH: 20
<212> TYPE: PRT
<213> ORGANISM: Artificial Sequence
<220> FEATURE:
```

```
<223> OTHER INFORMATION: ApoE mimetic peptide

<400> SEQUENCE: 64

Thr Glu Glu Leu Arg Val Arg Leu Ala Ser His Leu Arg Lys Leu Arg
1               5                   10                  15

Lys Arg Leu Leu
            20
```